US010548965B2

(12) United States Patent
Ross et al.

(10) Patent No.: US 10,548,965 B2
(45) Date of Patent: Feb. 4, 2020

(54) SYNERGISTIC CO-ADMINISTRATION OF COMPUTATIONALLY OPTIMIZED BROADLY REACTIVE ANTIGENS FOR HUMAN AND AVIAN H5N1 INFLUENZA

(71) Applicants: Oregon Health & Science University, Portland, OR (US); Sanofi Pasteur, Inc., Swiftwater, PA (US)

(72) Inventors: Ted Milburn Ross, Watkinsville, GA (US); Tim Alefantis, Springbrook Township, PA (US); Donald Martin Carter, Athens, GA (US); Christopher Austin Darby, Port Saint Lucie, FL (US); Harold Kleanthous, Chelmsford, MA (US)

(73) Assignees: Oregon Health & Science University, Portland, OR (US); Sanofi Pasteur, Inc., Swiftwater, PA (US)

( * ) Notice: Subject to any disclaimer, the term of this patent is extended or adjusted under 35 U.S.C. 154(b) by 176 days.

(21) Appl. No.: 15/537,109

(22) PCT Filed: Dec. 18, 2015

(86) PCT No.: PCT/US2015/066890
§ 371 (c)(1),
(2) Date: Jun. 16, 2017

(87) PCT Pub. No.: WO2016/100926
PCT Pub. Date: Jun. 23, 2016

(65) Prior Publication Data
US 2019/0111126 A1    Apr. 18, 2019

Related U.S. Application Data

(60) Provisional application No. 62/094,795, filed on Dec. 19, 2014.

(51) Int. Cl.
*A61K 39/145*   (2006.01)
*A61K 39/00*   (2006.01)

(52) U.S. Cl.
CPC .... *A61K 39/145* (2013.01); *A61K 2039/5252* (2013.01); *A61K 2039/5254* (2013.01); *A61K 2039/5258* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| 2012/0064117 A1 | 3/2012 | Ross et al. |
| 2013/0183342 A1 * | 7/2013 | Ross ............... C07K 14/11 424/210.1 |

FOREIGN PATENT DOCUMENTS

| WO | 2009/150532 A1 | 12/2009 |
| WO | 2010/063033 A2 | 6/2010 |
| WO | 2012/047941 A2 | 4/2012 |
| WO | 2013/122827 A1 | 8/2013 |
| WO | WO/13/122827 | * 8/2013 |

OTHER PUBLICATIONS

Yang et al., Multiple-Clade H5N1 Influenza Split Vaccine Elicits Broad Cross Protection against Lethal Influenza Virus Challenge in Mice by Intranasal Vaccination, 2012, PLoS One, vol. 7, No. 1, pp. 1-8.*
International Search Report and Written Opinion dated Mar. 11, 2016 from International Application No. PCT/US2015/066890, pp. 1-13.
Extended European Search Report dated Apr. 13, 2018 from European Patent Application No. 15871239.8, 6 pages.
European Patent Office Communication dated Mar. 18, 2019 from European Patent Application No. 15871239.8 (Primary Examiner, Wolfram Meyer), 5 pages.
Giles et al., "A computationally optimized broadly reactive antigen (COBRA) based H5N1 VLP vaccine elicits broadly reactive antibodies in mice and ferrets", Vaccine, Apr. 5, 2011, vol. 29, No. 16, pp. 3043-3054.

* cited by examiner

*Primary Examiner* — Benjamin P Blumel
(74) *Attorney, Agent, or Firm* — MH2 Technology Law Group, LLP

(57) ABSTRACT

The present invention provides co-administration (e.g., immunogenic cocktail and/or prime-boost regimens) of computationally optimized H5N1 influenza hemagglutinin (HA) polypeptides that. Co-administration of the optimized H5N1 influenza hemagglutinin (HA) polypeptides facilitates synergistic neutralization of viral infection and provides for improved protective immunity (e.g., a broad reactive immune response) to multiple H5N1 influenza virus clades and strains.

23 Claims, 11 Drawing Sheets

Specification includes a Sequence Listing.

H1N1 COBRA Prime/Boost

FIG. 1A

H1N1 COBRA Prime/Boost

Cocktail H1N1 COBRA

FIG. 2A

Cocktail H1N1 COBRA

SEQUENCE LISTING

```
<160> NUMBER OF SEQ ID NOS: 6

<210> SEQ ID NO 1
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45
```

-continued

```
Leu Glu Lys Thr His Asn Gly Lys Leu Cys Asp Leu Asp Gly Val Lys
 50                  55                  60
Pro Leu Ile Leu Arg Asp Cys Ser Val Ala Gly Trp Leu Leu Gly Asn
 65                  70                  75                  80
Pro Met Cys Asp Glu Phe Ile Asn Val Pro Glu Trp Ser Tyr Ile Val
                 85                  90                  95
Glu Lys Ala Ser Pro Ala Asn Asp Leu Cys Tyr Pro Gly Asp Phe Asn
                100                 105                 110
Asp Tyr Glu Glu Leu Lys His Leu Leu Ser Arg Ile Asn His Phe Glu
                115                 120                 125
Lys Ile Gln Ile Ile Pro Lys Ser Ser Trp Ser Asn His Glu Ala Ser
130                 135                 140
Ser Gly Val Ser Ser Ala Cys Pro Tyr Gln Gly Lys Ser Ser Phe Phe
145                 150                 155                 160
Arg Asn Val Val Trp Leu Ile Lys Lys Asn Ser Ala Tyr Pro Thr Ile
                165                 170                 175
Lys Arg Ser Tyr Asn Asn Thr Asn Gln Glu Asp Leu Leu Val Leu Trp
                180                 185                 190
Gly Ile His His Pro Asn Asp Ala Ala Glu Gln Thr Lys Leu Tyr Gln
                195                 200                 205
Asn Pro Thr Thr Tyr Ile Ser Val Gly Thr Ser Thr Leu Asn Gln Arg
210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
                275                 280                 285
Asn Cys Asn Thr Lys Cys Gln Thr Pro Met Gly Ala Ile Asn Ser Ser
                290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Arg Arg Lys Lys Arg Gly Leu Phe Gly Ala Ile
                340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Lys
                370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
                420                 425                 430
Gly Phe Leu Asp Val Trp Thr Tyr Asn Ala Glu Leu Leu Val Leu Met
                435                 440                 445
Glu Asn Glu Arg Thr Leu Asp Phe His Asp Ser Asn Val Lys Asn Leu
450                 455                 460
Tyr Asp Lys Val Arg Leu Gln Leu Arg Asp Asn Ala Lys Glu Leu Gly
```

```
        465                 470                 475                 480
Asn Gly Cys Phe Glu Phe Tyr His Lys Cys Asp Asn Glu Cys Met Glu
                    485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 2
<211> LENGTH: 1736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggaaaaga tcgtgctgct gctggccatc gtgtccctgg tgaagagcga ccagatttgc      60
attggctacc acgccaacaa tagcacagag caggtggaca ccatcatgga gaaaaacgtg     120
accgtgaccc acgcccagga catcctggag aaaacccaca acggcaagct gtgtgacctg     180
gacggcgtga agcccctgat cctgagagac tgctccgtgg ccggctggct gctgggcaac     240
cccatgtgtg acgagttcat caacgtgccc gagtggagct acatcgtgga aaggccagc     300 cccgccaacg acctgtgcta ccccggcgac ttcaacgact acgaggagct gaagcacctg     360
ctgtcccgga tcaaccactt cgagaagatc cagatcatcc caagagcag ctggagcaac     420 cacgaggcca gcagcggcgt gtccagcgcc tgcccctacc agggcaagag cagcttcttc     480
cggaacgtgg tctggctgat caagaagaac tctgcctatc caccatcaa gcggagctac     540 aacaacacca ccaggagga tctgctggtc ctgtggggca ccaccaccc caacgacgcc     600 gccgagcaga ccaagctgta ccagaacccc accacctaca tcagcgtggg caccagcacc     660
ctgaaccagc ggctggtgcc aagatcgcc accggtcca agtgaacgg ccagagcggc      720 cggatggaat tcttctggac catcctgaag cccaacgatg ccatcaactt cgagagcaac     780
ggcaacttca tcgcccccga gtacgcctac aagatcgtga agaagggcga cagcgccatc     840
atgaagagcg agctggaata cggcaactgc aacaccaagt gccagacccc catgggcgcc     900
atcaacagca gcatgccctt ccacaacatc caccccctga catcggcga gtgccccaag     960 tacgtgaaga gcaacaggct ggtgctggcc accggcctgc ggaacagccc cagcgggag    1020 cggcggagga gaagcgggg cctgttcggc gccatcgccg gcttcatcga gggcggctgg    1080
cagggcatgg tggacgggtg gtacggctac caccacagca tgagcaggg cagcggctac    1140 gccgccgaca agagagcac ccagaaggcc atcgacggcg tcaccaacaa ggtgaacagc    1200
atcatcgaca agatgaacac ccagttcgag gccgtgggcc gggagttcaa caacctggaa    1260
cggcggatcg agaacctgaa caagaaaatg gaagatggct tcctggacgt gtggacctac    1320
aacgccgaac tcctggtgct gatggaaaac gagcggaccc tggacttcca cgacagcaac    1380
gtgaagaacc tgtacgacaa agtgcggctg cagctgcggg acaacgccaa agagctgggc    1440
```

```
aacggctgct tcgagttcta ccacaagtgc gacaacgagt gcatggaaag cgtgcggaac   1500
ggcacctacg actacccca gtacagcgag gaagcccggc tgaagcggga ggaaatcagc   1560
ggcgtgaaac tggaaagcat cggcacctac cagatcctga gcatctacag caccgtggcc   1620
agcagcctcg ctctggccat tatggtggcc ggcctgagcc tgtggatgtg cagcaacggc   1680
agcctgcagt gccggatcgg atccagatct gctagcgtcg actctagatt aattaa      1736
```

<210> SEQ ID NO 3
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
```

Tyr Val Lys Ser Asn Arg Leu Val Leu Ala Thr Gly Leu Arg Asn Ser
305                 310                 315                 320
                325                 330                 335

Pro Gln Arg Glu Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
            370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
            450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
            530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 4
<211> LENGTH: 1739
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggagaaga tcgtgctgct gctggccatc gtgtccctgg tgaagagcga ccagatttgc      60
atcggctacc acgccaacaa tagcaccgag caagtggaca ccatcatgga gaaaaacgtg     120
accgtgaccc acgctcagga catcctcgaa aaacccaca acggcaagct gtgcgatctg      180
gacggcgtga agcccctgat cctgagagac tgcagcgtgg ccggctggct gctgggcaat     240
cccatgtgcg acgagttcat caacgtgccc gagtggagct acatcgtgga aaggccaac      300 cccgccaacg acctgtgcta ccccggcaac ttcaacgact acgaggagct gaagcacctg     360
ctgagccgga tcaaccactt cgagaagatc cagatcatcc ccaagagcag ctggagcgac     420
catgaggcaa gcagcggcgt gtccagcgcc tgccccctacc agggcaagtc cagcttcttc     480
cgcaacgttg tgtggctgat caagaagaac agcgcctacc ccaccatcaa gcggagctac     540

-continued

| | |
|---|---|
| aacaacacca accaggagga cctgctggtc ctgtggggca tccaccaccc caacgacgcc | 600 |
| gccgagcaga cccggctgta ccagaacccc accacctaca tctctgtggg caccagcacc | 660 |
| ctgaaccagc ggctggtgcc caagatcgcc acccggagca aggtgaacgg ccagagcggc | 720 |
| cggatggagt tcttctggac catcctgaag cccaacgatg ccatcaactt cgagagcaac | 780 |
| ggcaacttca tcgcccccga gtacgcctac aagatcgtga agaagggcga cagcgccatc | 840 |
| atgaagtccg agctggagta cggcaactgt aacaccaagt gccagacccc catgggcgcc | 900 |
| atcaacagca gcatgcccct tccacaacatc cacccctga ccatcggcga gtgccccaag | 960 |
| tacgtgaaga gcaacaggct ggtgctggcc accggcctga aaacagccc ccagagagag | 1020 |
| cggagaagaa agagaggcct gttcggcgcc attgccggct tcatcgaggg cggctggcag | 1080 |
| ggcatggtgg acgggtggta cggctaccac cactccaacg agcagggcag cggctacgcc | 1140 |
| gccgacaaag agagcaccca gaaagctatc gacgcgtga ccaacaaagt gaacagcatc | 1200 |
| atcgacaaga tgaatacccca gttcgaggcc gtgggcagag agttcaacaa cctggaaaga | 1260 |
| agaatcgaga acctgaacaa gaaaatggaa gatggctttc tggatgtgtg gacctacaac | 1320 |
| gccgagctgc tggtgctgat ggaaaacgag cggacccctgg acttccacga cagcaacgtg | 1380 |
| aagaatctgt acgacaaagt gcggctgcag ctgagagaca cgccaaaga gctgggcaac | 1440 |
| ggctgcttcg agttctacca caagtgcgac aatgagtgca tggaaagcgt gcggaacggc | 1500 |
| acctacgact ccccccagta cagcgaggaa gcccggctga agagaaga gatttccggc | 1560 |
| gtgaagctgg aaagcatcgg cacctaccag atcctgagca tctacagcac cgtggccagc | 1620 |
| agcctggccc tggccatcat ggtggccggc ctgagcctgt ggatgtgcag caacggcagc | 1680 |
| ctgcagtgcc ggatctgcat cggatccaga tctgctagcg tcgactctag attaattaa | 1739 |

```
<210> SEQ ID NO 5
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Ser Pro Ser Phe Phe
```

```
              145                 150                 155                 160
Arg Asn Val Val Trp Leu Ile Lys Lys Asn Asn Thr Tyr Pro Thr Ile
                    165                 170                 175
Lys Arg Ser Tyr Asn Asn Thr Asn Gln Glu Asp Leu Leu Val Leu Trp
                180                 185                 190
Gly Ile His His Pro Asn Asp Ala Ala Glu Gln Thr Arg Leu Tyr Gln
                195                 200                 205
Asn Pro Thr Thr Tyr Ile Ser Val Gly Thr Ser Thr Leu Asn Gln Arg
            210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                    245                 250                 255
Phe Glu Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
                275                 280                 285
Asn Cys Asn Thr Lys Cys Gln Thr Pro Ile Gly Ala Ile Asn Ser Ser
            290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                    325                 330                 335
Pro Gln Arg Glu Ser Arg Arg Lys Lys Arg Gly Leu Phe Gly Ala Ile
                340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Lys
            370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                    405                 410                 415
Asn Asn Leu Glu Arg Arg Ile Glu Asn Leu Asn Lys Lys Met Glu Asp
                420                 425                 430
Gly Phe Leu Asp Val Trp Thr Tyr Asn Ala Glu Leu Leu Val Leu Met
                435                 440                 445
Glu Asn Glu Arg Thr Leu Asp Phe His Asp Ser Asn Val Lys Asn Leu
            450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                    485                 490                 495
Ser Val Arg Asn Gly Thr Tyr Asp Tyr Pro Gln Tyr Ser Glu Glu Ala
                500                 505                 510
Arg Leu Lys Arg Glu Glu Ile Ser Gly Val Lys Leu Glu Ser Ile Gly
                515                 520                 525
Thr Tyr Gln Ile Leu Ser Ile Tyr Ser Thr Val Ala Ser Ser Leu Ala
            530                 535                 540
Leu Ala Ile Met Val Ala Gly Leu Ser Leu Trp Met Cys Ser Asn Gly
545                 550                 555                 560
Ser Leu Gln Cys Arg Ile Cys Ile
                565
```

```
<210> SEQ ID NO 6
<211> LENGTH: 1707
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggaaaaga tcgtgctgct gctggctatc gtgagcctgg tgaagagcga ccagatttgc      60
atcggctacc acgccaacaa cagcaccgag caggtggaca ccatcatgga aaagaacgtc     120
accgtgaccc acgcccagga catcctggaa aagacccaca cggcaagct gtgcgacctg      180
gacggcgtga agcccctgat cctgagggac tgcagcgtgg ccggctggct gctgggcaac     240
cccatgtgcg acgagttcat caacgtgccc gagtggagct acatcgtgga aaggccaac      300
cccgccaacg acctgtgcta ccccggcaac ttcaacgact acgaggaact gaagcacctg     360
ctgtccagga tcaaccactt cgagaagatc cagatcatcc caagagcag ctggtccgac      420
cacgaggcca gcagcggcgt gagcagcgcc tgcccatacc agggcagccc cagcttcttc     480
agaaacgtgg tgtggctgat caagaagaac aacacctacc caccatcaa gaggtcctac     540
aacaacacca accaggaaga tctgctggtc ctgtggggca tccaccaccc taatgacgcc     600
gccgaacaga ccaggctgta ccagaacccc accacctaca tcagcgtggg cacaagcacc     660
ctgaaccaga ggctggtgcc caagatcgcc accaggtcca aggtgaacgg acagtccggc     720
aggatggaat tcttctggac catcctgaag cctaacgacg ccatcaactt cgagagcaac     780
ggcaactta tcgccccga gtacgcctac aagatcgtga agaagggcga cagcgccatc      840
atgaagagcg agctggaata cggcaactgc aacaccaagt gccagacccc catcggcgcc     900
atcaacagca gcatgccctt ccacaacatc caccccctga ccatcggcga gtgccccaag     960
tacgtgaaga gcaacaggct ggtgctggcc accggcctga ggaacagccc ccagagagag    1020
agcagaagaa agaagagggg cctgttcggc gctatcgccg gcttcatcga gggcggctgg    1080
cagggcatgg tggacgggtg gtacggctac caccactcta acgagcaggg cagcggctac    1140
gccgccgaca agagagcac ccagaaggcc atcgacggcg tcaccaacaa ggtgaacagc     1200
atcatcgaca gatgaacac ccagttcgag gccgtgggca gagagttcaa caacctggaa     1260
aggcggatcg agaacctgaa caagaaaatg gaagatggct tcctggacgt gtggacctac    1320
aacgccgagc tgctggtgct gatggaaaac gagaggaccc tggacttcca cgacagcaac    1380
gtgaagaacc tgtacgacaa agtgcggctg cagctgaggg acaacgccaa agagctgggc    1440
aacggctgct tcgagttcta ccacaagtgc gacaacgagt gcatggaaag cgtgaggaac    1500
ggcacctacg actaccccca gtacagcgag gaagccaggc tgaagaggga agagatcagc    1560
ggagtgaagc tggaaagcat cggcacctac cagatcctga gcatctacag caccgtcgcc    1620
agcagcctgg ccctggctat catggtggcc ggactgagcc tgtggatgtg cagcaacggc    1680
agcctgcagt gcaggatctg catctga                                        1707
```

SYNERGISTIC CO-ADMINISTRATION OF COMPUTATIONALLY OPTIMIZED BROADLY REACTIVE ANTIGENS FOR HUMAN AND AVIAN H5N1 INFLUENZA

CROSS REFERENCE TO RELATED APPLICATIONS

This application is a U.S. National Stage application of PCT/US2015/066890 filed 18 Dec. 2015, which claims the benefit of, and relies on the filing date of, U.S. provisional patent application No. 62/094,795, filed 19 Dec. 2014, the entire disclosure of which is herein incorporated by reference.

SEQUENCE LISTING

The instant application contains a Sequence Listing which has been submitted electronically in ASCII format and is hereby incorporated by reference in its entirety. Said ASCII copy, created on Dec. 11, 2015, is named 0171.0006-PCT_SL.txt and is 22,576 bytes in size.

BACKGROUND

Influenza is caused by a virus that attacks mainly the upper respiratory tract—the nose, throat and bronchi and rarely also the lungs. The infection usually lasts for about a week. It is characterized by sudden onset of high fever, myalgia, headache and severe malaise, non-productive cough, sore throat, and rhinitis. Most people recover within one to two weeks without requiring any medical treatment. However, in the very young, the elderly and people suffering from medical conditions such as lung diseases, diabetes, cancer, kidney or heart problems, influenza poses a serious risk. In these people, the infection may lead to severe complications of underlying diseases, pneumonia and death. Annual influenza epidemics are thought to result in between three and five million cases of severe illness and between 250,000 and 500,000 deaths every year around the world.

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (MI), proton ion-channel protein (M2), nucleoprotein (NP), polymerase basic protein 1 (PBI), polymerase basic protein 2 (PB2), polymerase acidic protein (PA), and nonstructural protein 2 (NS2). The HA, NA, MI, and M2 are membrane associated, whereas NP, PBI, PB2, PA, and NS2 are nucleocapsid associated proteins. The MI protein is the most abundant protein in influenza particles. The HA and NA proteins are envelope glycoproteins, responsible for virus attachment and penetration of the viral particles into the cell. Specifically, HA binds the influenza virus to cells with sialic acid-containing on surface structures on their membranes.

Both HA and NA proteins are the sources of the major immunodominant epitopes for virus neutralization and protective immunity, making them important components for prophylactic influenza vaccines. The genetic makeup of influenza viruses allows frequent minor genetic changes, known as antigenic drift. Thus, the amino acid sequence of the major antigens of influenza, particularly HA, is highly variable across groups, subtypes and strains.

Pandemic outbreaks of influenza are caused by the emergence of a pathogenic and transmissible virus to which the human population is immunologically naïve. Because the virus is new, the human population has little to no immunity against it. The virus spreads quickly from person-to-person worldwide. Three times in the last century, the influenza A viruses have undergone major genetic changes mainly in their H-component, resulting in global pandemics and large tolls in terms of both disease and deaths. The most infamous pandemic was "Spanish Flu" which affected large parts of the world population and is thought to have killed at least 40 million people in 1918-1919. More recently, two other influenza A pandemics occurred in 1957 ("Asian influenza") and 1968 ("Hong Kong influenza") and caused significant morbidity and mortality globally. In contrast to current influenza epidemics, these pandemics were associated with severe outcomes also among healthy younger persons, albeit not on such a dramatic scale as the "Spanish flu" where the death rate was highest among healthy young adults. Most recently, limited outbreaks of a new influenza subtype A (H5N1) directly transmitted from birds to humans have occurred in Hong Kong Special Administrative Region of China in 1997 and 2003. Recent outbreaks of highly pathogenic avian influenza (HPAI) of the H5N1 subtype are of particular concern because of the high mortality rate (60% case fatality rate) and novel subtype. Due to antigenic drift, and even more dramatic alterations known as antigenic shift, pandemic influenza antigens (e.g., the HA amino acid sequence of the pandemic strain) are highly unpredictable. Thus, vaccines have traditionally been unavailable until the later stages of a pandemic.

SUMMARY

The present invention provides, among other things, co-administration (i.e., prime-boost combinations or composition cocktails) of computationally optimized H5N1 influenza hemagglutinin (HA) polypeptides that, when presented to the immune system can elicit cross-clade HAI activity protective against challenge viruses from different clades and sub-clades. Without being bound by any particular theory, it is thought that each individual polypeptide elicits different sets of antibodies that bind to different antigenic regions of the HA molecule; but when co-administered (either as a prime-boost regimen or as a cocktail), they elicit antibodies that recognize divergent HA head epitopes that synergistically neutralize viral infection and provide for improved protective immunity (e.g., a broad reactive immune response) to multiple H5N1 influenza virus clades and sub-clades. The optimized HA polypeptides were developed through a series of HA protein alignments, and subsequent generation of consensus sequences based on thousands of human and avian H5N1 influenza isolates. In particular embodiments, the cross-clade protectiveness spans strains originating over at least the last 5, 6, 7, 8, 9, 11, 12, 15, 20, etc. years.

Provided herein are immunogenic compositions comprising combinations of at least two recombinant H5N1 influenza hemagglutinin (HA) polypeptides selected from the group consisting of: a recombinant, optimized influenza HA polypeptide comprising an amino acid sequence at least 99.8% identical to SEQ ID NO: 1, a recombinant, optimized influenza HA polypeptide comprising an amino sequence at least 99.6% identical to SEQ ID NO: 3, and a recombinant, optimized influenza HA polypeptide comprising an amino sequence at least 99% identical to SEQ ID NO: 5. Also provided herein are immunogenic compositions comprising a combination of at least two recombinant H5N1 influenza hemagglutinin (HA) polypeptides selected from the group consisting of: a recombinant, optimized influenza HA polypeptide comprising an amino acid sequence at least 99.8% identical to residues 2-566 of SEQ ID NO: 1, a recombinant, optimized influenza HA polypeptide comprising an amino acid sequence at least 99.6% identical to residues 2-567 of SEQ ID NO: 3, and a recombinant, optimized influenza HA polypeptide comprising an amino sequence is least 99% identical to amino acids 2-568 of SEQ ID NO: 5.

In some embodiments, the compositions described herein comprise (i) a first optimized influenza HA polypeptide comprising an amino acid sequence at least 99.8% identical to SEQ ID NO: 1, and (ii) second optimized influenza HA polypeptide comprising an amino sequence at least 99.6% identical to SEQ ID NO: 3. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 3. In some embodiments, the optimized influenza HA polypeptides lack the N-terminal methionine residue.

In some embodiments, the compositions described herein comprise (i) a first optimized influenza HA polypeptide comprising an amino acid sequence at least 99.8% identical to SEQ ID NO: 1, and (ii) second optimized influenza HA polypeptide comprising an amino sequence at least 99% identical to SEQ ID NO: 5. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 5. In some embodiments, the optimized influenza HA polypeptides lack the N-terminal methionine residue.

In some embodiments, the compositions described herein comprise (i) a first optimized influenza HA polypeptide comprising an amino acid sequence at least 99.6% identical to SEQ ID NO: 3, and (ii) second optimized influenza HA polypeptide comprising an amino sequence at least 99% identical to SEQ ID NO: 5. In some embodiments, the compositions comprise at least two different optimized influenza HA polypeptides, wherein the amino acid sequence of the polypeptides comprises no more than two, or no more than one substitution relative to SEQ ID NO: 3 or SEQ ID NO: 5. In some embodiments, the optimized influenza HA polypeptides lack the N-terminal methionine residue.

In some embodiments, the compositions described herein comprise (i) a first optimized influenza HA polypeptide comprising an amino acid sequence at least 99.8% identical to SEQ ID NO: 1, a (ii) second optimized influenza HA polypeptide comprising an amino sequence at least 99.6% identical to SEQ ID NO: 3, and (iii) a third optimized influenza HA polypeptide comprising an amino acid sequence at least 99% identical to SEQ ID NO: 5. In some embodiments, the compositions comprise at least three different optimized influenza HA polypeptides, wherein the amino acid sequence of the polypeptides comprises no more than three, no more than two, or no more than one substitution relative to SEQ ID NO: 1, SEQ ID NO: 3, or SEQ ID NO: 5. In some embodiments, the optimized influenza HA polypeptides lack the N-terminal methionine residue.

In some embodiments, the compositions comprise a combination of recombinant H5N1 influenza HA polypeptides consisting of a recombinant, optimized influenza HA polypeptide comprising an amino acid sequence at least 99.8% identical to residues 2-566 of SEQ ID NO: 1 and a recombinant, optimized influenza HA polypeptide comprising an amino acid sequence at least 99.6% identical to residues 2-567 of SEQ ID NO: 3. In some embodiments, the compositions comprise a combination of recombinant H5N1 influenza HA polypeptides consisting of a recombinant, optimized influenza HA polypeptide comprising an amino acid sequence at least 99.8% identical to residues 2-566 of SEQ ID NO: 1 and a recombinant, optimized influenza HA polypeptide comprising an amino sequence is least 99% identical to amino acids 2-568 of SEQ ID NO: 5. In some embodiments, the compositions comprise a combination of recombinant, optimized H5N1 influenza HA polypeptides consisting of a recombinant, optimized influenza HA polypeptide comprising an amino acid sequence at least 99.6% identical to residues 2-567 of SEQ ID NO: 3 and a recombinant, optimized influenza HA polypeptide comprising an amino sequence is least 99% identical to amino acids 2-568 of SEQ ID NO: 5.

Isolated nucleic acid molecules and vectors encoding the recombinant, optimized HA polypeptides are also provided by the present disclosure. In some embodiments, the nucleic acid molecules and vectors encoding the recombinant, optimized influenza HA polypeptides comprise the nucleotide sequence of SEQ ID NO: 2 SEQ ID NO: 4, or SEQ ID NO: 6. Further provided are isolated cells comprising such vectors. Also provided are recombinant influenza viruses comprising the computationally optimized recombinant HA polypeptides described herein.

Also provided are influenza virus-like particles (VLPs), inactivated influenza viruses or virions, and fusion proteins comprising the optimized HA polypeptides disclosed herein, which VLPs and viruses/virions and fusion proteins of the individual HA polypeptides can be mixed or combined into the cocktails described above.

Further provided are compositions that include the cocktails of the optimized influenza HA polypeptides, fusion proteins, viruses/virions or VLPs disclosed herein in a pharmaceutically acceptable carrier. Methods of eliciting an immune response against influenza virus in a subject by administering the disclosed immunogenic compositions of cocktails of optimized influenza HA polypeptides, fusion proteins, virus or VLPs are also provided by the present disclosure.

Also provided are methods of immunizing a subject against H5N1 influenza virus by co-administering to the subject the optimized HA polypeptides disclosed herein, either as part of a prime-boost regimen or as a cocktail of two or three of the optimized HA polypeptides. In certain embodiments, the methods comprise immunizing a subject against H5N1 influenza virus by administering to the subject a composition or compositions comprising the combinations or cocktails of the optimized H5N1 influenza HA polypeptides disclosed herein. Further provided are methods of immunizing a subject against H5N1 influenza virus by administering to the subject a priming vaccine comprising a first optimized H5N1 influenza HA polypeptide as described herein followed by a boosting vaccine comprising a second optimized H5N1 influenza HA polypeptide as described herein, where the second optimized H5N1 influenza HA polypeptide is different than the first optimized H5N1 influenza HA polypeptide. In some embodiments, the priming vaccine is a live, attenuated influenza virus (e.g., temperature sensitive virus).

The foregoing and other objects, features, and advantages of the invention will become more apparent from the following detailed description, which proceeds with reference to the accompanying figures.

BRIEF DESCRIPTION OF THE DRAWING

The Drawing included herein, which is comprised of the following Figures, is for illustration purposes only not for limitation.

FIGS. 2A-B. Schematic of three dimensional structure of trimerized H5N1 COBRA HA proteins. FIG. 2A shows the predicted structural model of the H5N1 COBRA HA sequences. HA sequences were downloaded encoded NCBI GenBank and GISAID to develop the COBRA HA sequences. Each COBRA HA structure presented was generated using the 3D-JIGSAW algorithm based on and renderings were performed using MacPyMol. FIG. 2B shows the amino acid positions in major HA antigenic sites that differ between the three COBRA H5N1 HA sequences.

FIGS. 4A-D. Highly pathogenic H5N1 influenza virus challenge of mice. BALB/c mice (5 mice/group) vaccinated at weeks 0 and 4 with each vaccine plus alum adjuvant were infected with $5 \times 10^6$ PFU of the highly pathogenic clade 2.1 H5N1 virus A/Whooperswan/Mongolia/244/2005 (WS/05) or the clade 1 H5N1 virus A/Vietnam/1203/2004 (VN/04). Mice were monitored daily for weight loss (A and C) and viral lung titers on selected mice on day 3 post-infection (B and D).

FIG. 5. Viral lung titers in mice vaccinated with a single vaccination. BALB/c mice (5 mice/group) vaccinated one time with a 3 ug dose with each vaccine plus alum adjuvant and then were infected with $5 \times 10^6$ PFU with the clade 1 H5N1 virus A/Vietnam/1203/2004 (VN/04). Mice were monitored daily for weight loss (data not shown) and viral lung titers on selected mice on days 2 and 3 post-infection.

FIGS. 6A-D. Highly pathogenic H5N1 influenza virus challenge of mice. BALB/c mice (5 mice/group) vaccinated one time with a 0.6 ug dose with each vaccine plus alum adjuvant were infected with 5×106 PFU of WS/05 or VN/04. Mice were monitored daily for weight loss (A and B) and viral lung titers on selected mice on days 2 and 3 post-infection (C and D).

DEFINITIONS

Figure 1D:
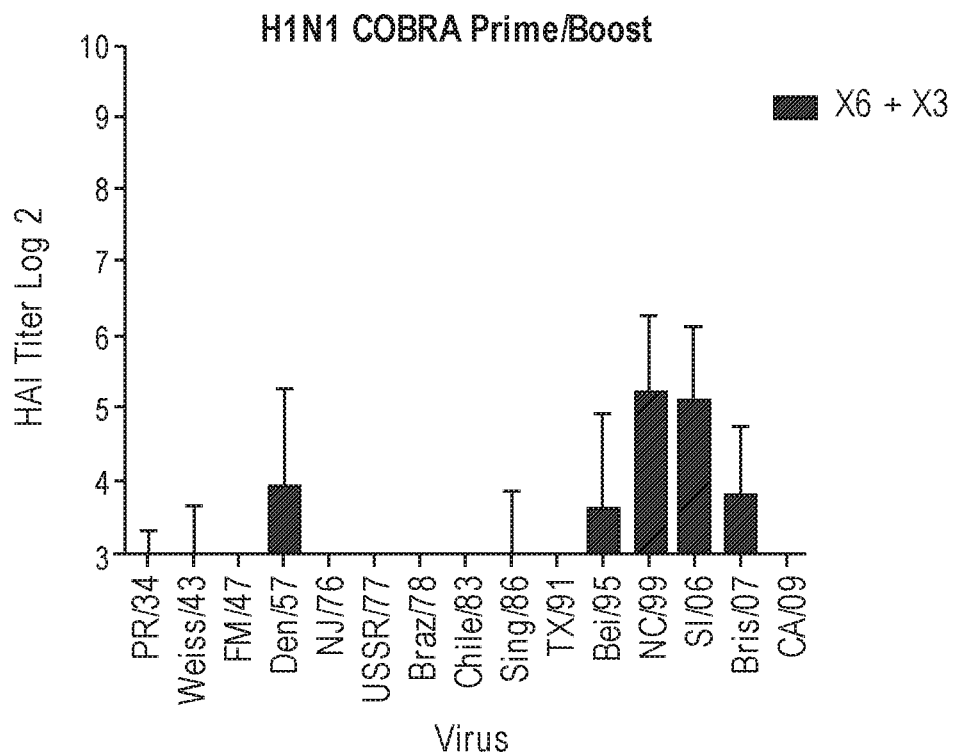
FIGS. 1A-C. Schematic of the Design of the H5N1 COBRA HA proteins. A phylogenetic tree was inferred from hemagglutinin amino acid sequences using the maximum likelihood method and clade/sub-clade groupings were identified. The first generation, human COBRA-2 (upper left) was designed using sequences identified in clade 2 from human infections (between 2005-2007) and has previously been described (Giles et al. 2010. Vaccine). Primary consensus sequences were generated for each outbreak group. Secondary consensus sequences were then generated for each subclade using the primary sequences as inputs. The secondary consensus sequences were then aligned and the resulting consensus, designated COBRA, was generated. The second generation of H5N1 COBRA HA proteins were designed using clade 2 isolates from both human and avian infections (upper right) and using all HA H5N1 sequences from all clades (2005-2010) in the NCBI and GASIAD databases.
Figure 1D:
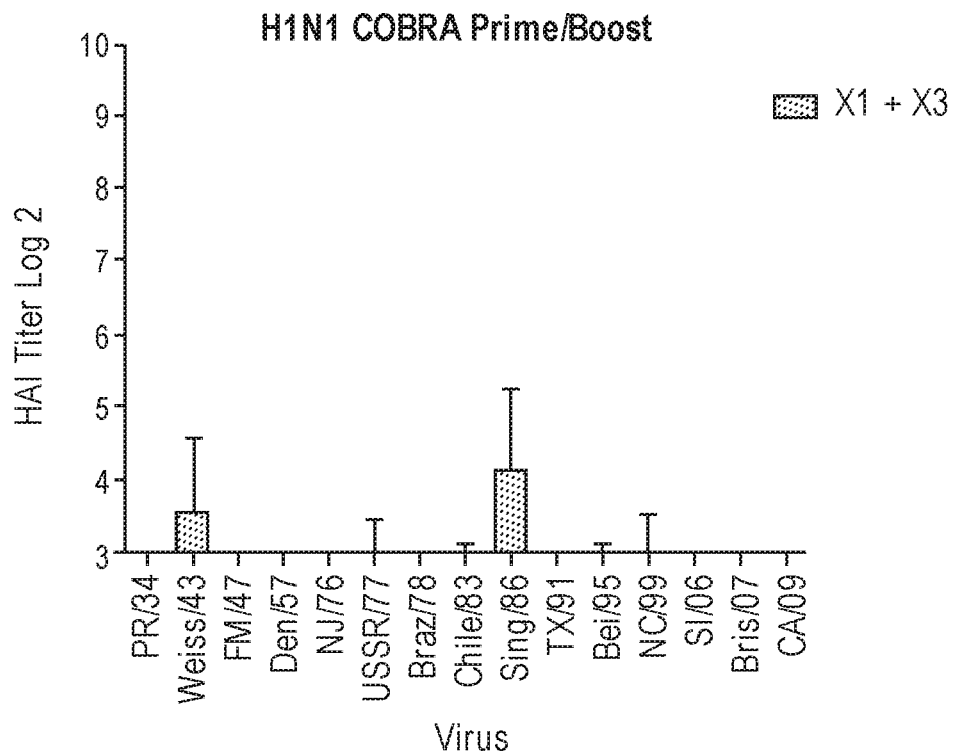
Figure 1G:
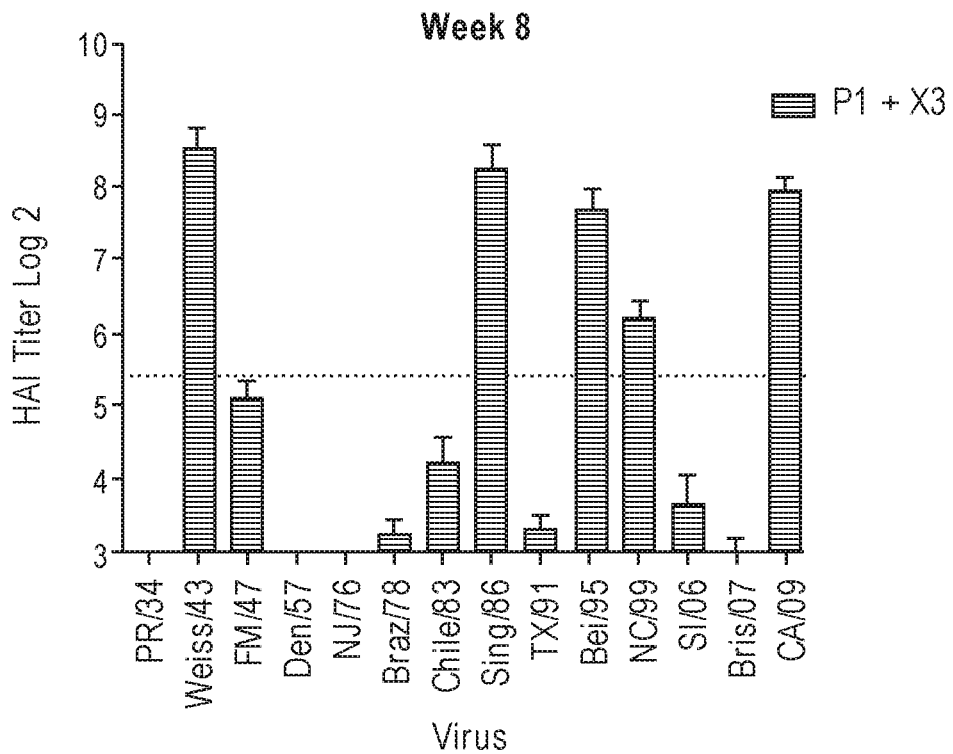
Figure 1H:
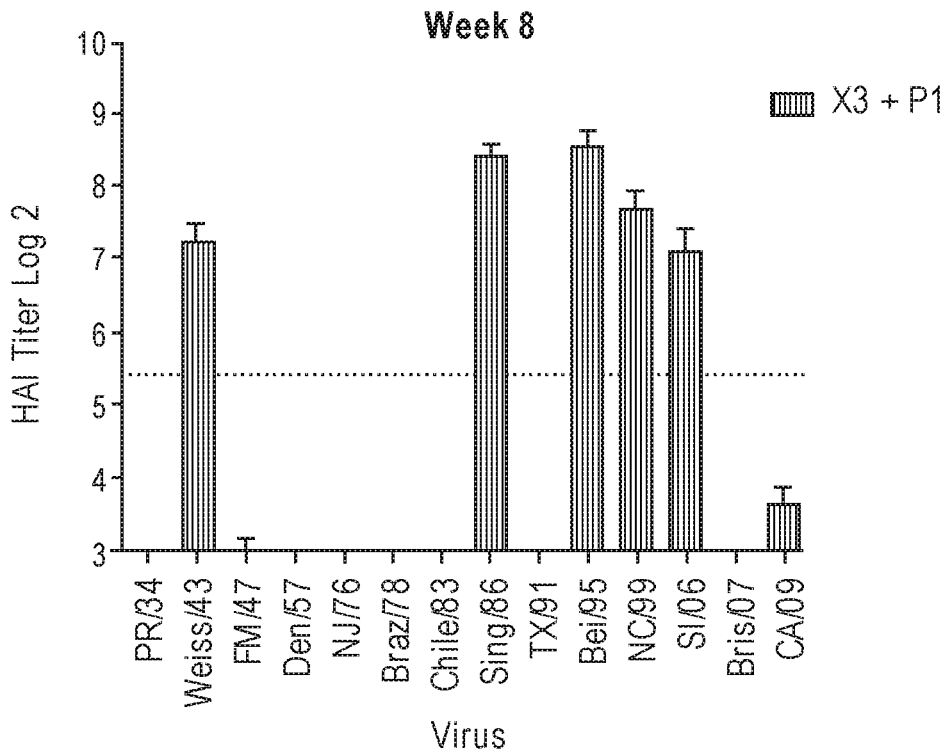
Figure 1I:
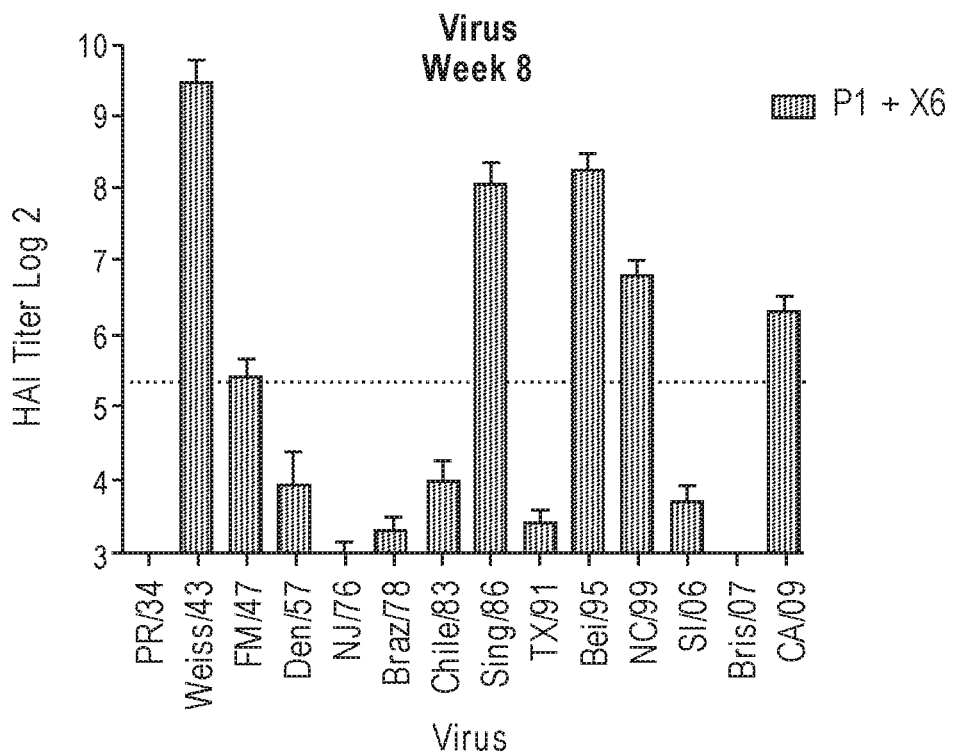
Figure 1J:
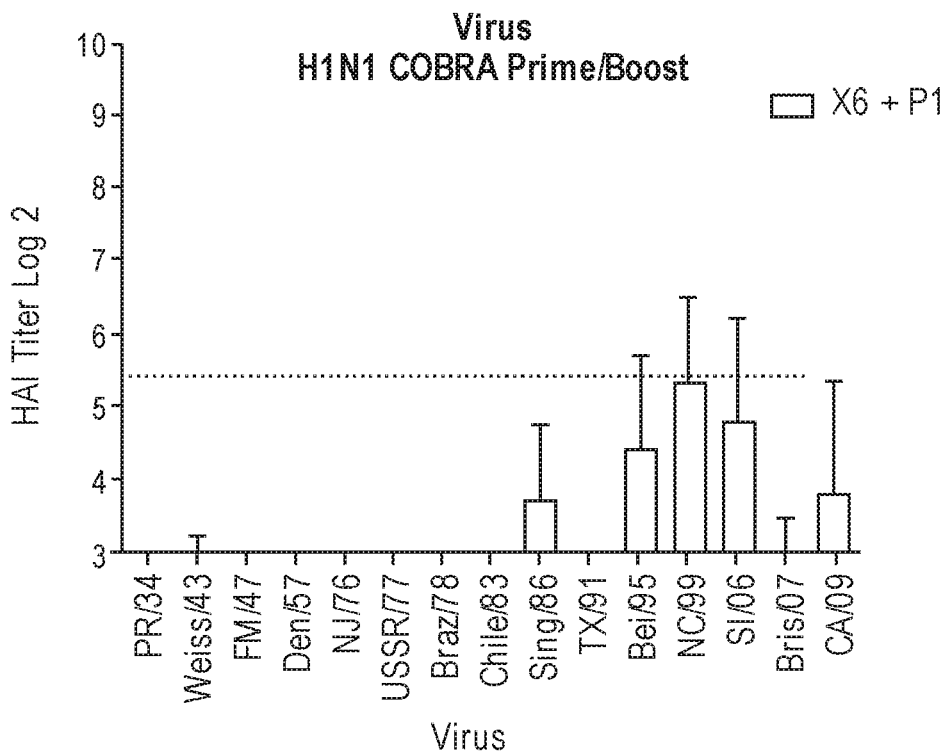
Figure 1K:
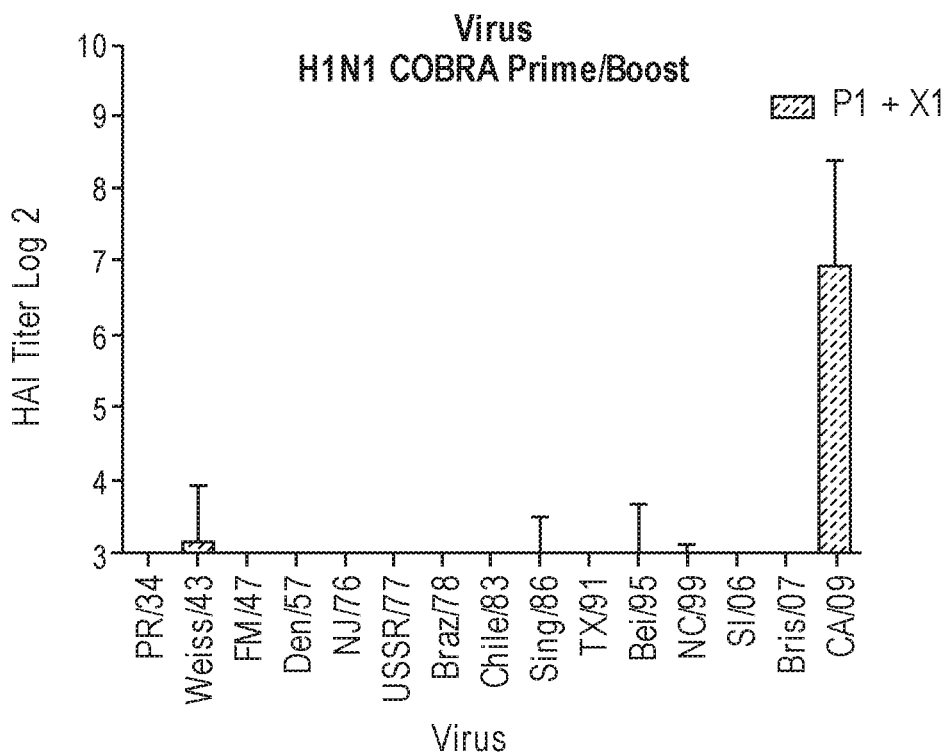
Figure 1L:
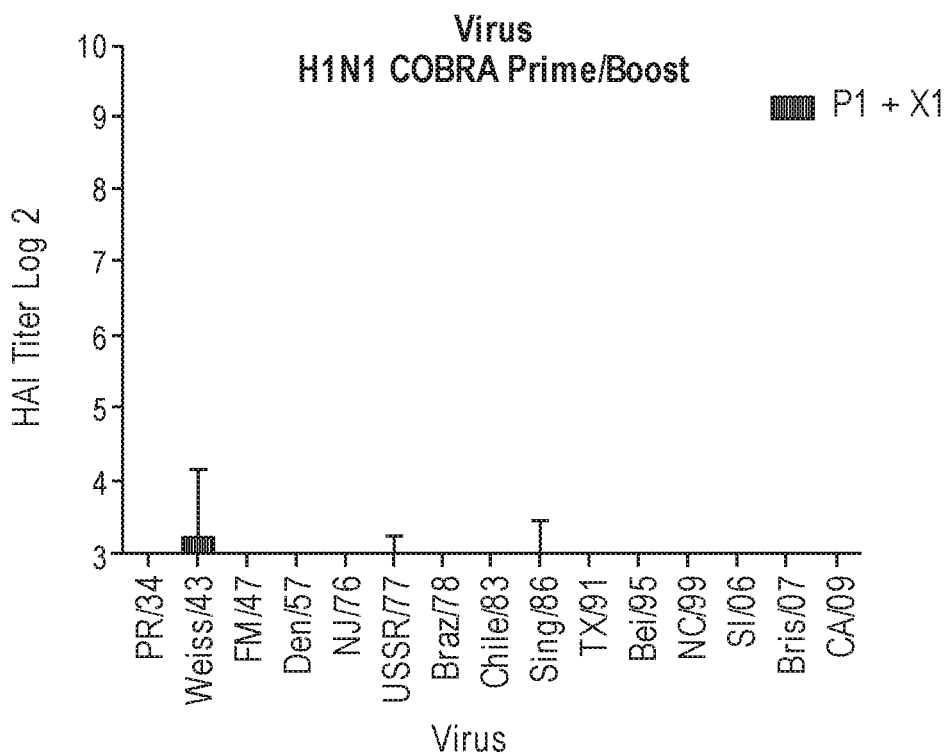

In order for the present invention to be more readily understood, certain terms are first defined below. Additional definitions for the following terms and other terms are set forth through the specification.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Adjuvant: As used herein, the term "adjuvant" refers to a substance or vehicle that non-specifically enhances the immune response to an antigen. Adjuvants can include a suspension of minerals (alum, aluminum salts, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as lipids and costimulatory molecules. Exemplary biological adjuvants include AS04 (Didierlaurent, A. M. et al, *J. Immunol.*, 2009, 183: 6186-6197), IL-2, RANTES, GM-CSF, TNF-α, IFN-γ, G-CSF, LFA-3, CD72, B7-1, B7-2, OX-40L and 41 BBL.

Administer: As used herein, "administering" a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Antibody: As used herein, the term "antibody" refers to a polypeptide that includes canonical immunoglobulin sequence elements sufficient to confer specific binding to a particular target antigen. In some embodiments, as used herein, the term "antibody" also refers to an "antibody fragment" or "antibody fragments", which includes a portion of an intact antibody, such as, for example, the antigen-binding or variable region of an antibody. Examples of "antibody fragments" include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable ($V_H$) domain (located at the tips of the Y structure), followed by three constant domains: $C_H1$, $C_H2$, and the carboxy-terminal $C_H3$ (located at the base of the Y's stem). A short region, known as the "switch", connects the heavy chain variable and constant regions. The "hinge" connects $C_H2$ and $C_H3$ domains to the rest of the antibody. Two disulfide bonds in this hinge region connect the two heavy chain polypeptides to one another in an intact antibody. Each light chain is comprised of two domains—an amino-terminal variable ($V_L$) domain, followed by a carboxy-terminal constant ($C_L$) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $C_H2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain ($\kappa$ and $\lambda$) classes, several heavy chain (e.g., $\mu$, $\gamma$, $\alpha$, $\varepsilon$, $\delta$) classes, and certain heavy chain subclasses ($\alpha1$, $\alpha2$, $\gamma1$, $\gamma2$, $\gamma3$, and $\gamma4$). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, camelid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a gly-can, a payload [e.g., a detectable moiety, a therapeutic moiety, a catalytic moiety, etc.], or other pendant group [e.g., poly-ethylene glycol, etc.]).

Antigen: As used herein, the term "antigen", refers to an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments of the disclosed compositions and methods, influenza HA H5N1 protein is an antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Clade: As used herein, the terms "clade" or "clades" refer to the World Health Organization (WHO) updated unified nomenclature system for pathogenic H5N1 influenza viruses (http://www.who.int/influenza/gisrs_laboratory/h5n1_nomenclature/en/). Phylogenetic analysis was performed using a variety of approaches on all of the publicly available H5 HA sequences that have evolved from the A/goose/Guangdong/1996 H5N1 virus. The initial results showed that the currently circulating H5N1 viruses could be effectively grouped into numerous virus "clades" based on the phylogenetic characterization and sequence homology of the HA gene. Based on criteria used to distinguish various groups of the H5 hemagglutinin (HA) gene, the system has formally identified 20 distinct clades of the virus since its inception in early 2008. These clades are defined as meeting the following three specific clade definition criteria: sharing of a common (clade-defining) node in the phylogenetic tree; monophyletic grouping with a bootstrap value of ≥60 at the clade-defining node (after 1000 neighbor-joining bootstrap replicates); and average percentage pairwise nucleotide distances between and within clades of >1.5% and <1.5%, respectively. As the viruses within these clades continue to evolve, new sublineages or subclades (potential H5N1 clades) periodically emerge. Once these sublineages meet the same three specific clade definition criteria as the initial clades (listed above), they are designated as separate clades. These new clades are defined as second, third or fourth-order clades and assigned a numerical 'address' which links them to their original clade using a hierarchical decimal numbering system. For example, within the distinct clade 2.3, third order clades meeting the clade definition were designated as clades 2.3.1 and 2.3.2 and so on. More recently, a new monophyletic clade was identified within clade 2.3.2 and assigned a fourth order designation as clade 2.3.2.1. Currently circulating clades include 1, 2.1.3, 2.2, 2.2.1, 2.3.2, 2.3.4 and 7. The immunogenic compositions described herein elicit cross-clade protective immunity, meaning that they generate an immunizing antibody titer (e.g., greater than or equal to 1:40 as measured by hemagglutination inhibition assays as described herein) against 2 or more, 3 or more, 4 or more, 5 or more, etc. distinct clades; for example, an immunogenic composition comprising a cocktail of the three computationally optimized H5N1 HA antigens set forth in Table 1 generates an immunizing antibody titer against H5N1 influenza viruses of clade 1, clade 2, clade 4, clade 5, clade 7, and subclades thereof (e.g., 2.1.3, 2.1.3.2, 2.2, 2.2.1, 2.2.2, 2.3.2, 2.3.2.1, 2.3.4, 7.2, etc.).

Co-administer: As used herein, "co-administer" and "co-administering" refer to the administration of at least two different optimized influenza HA proteins to a subject. In some embodiments, the at least two optimized influenza HA proteins are administered at the same time as a combination or cocktail. In some embodiments, a first and second optimized influenza HA protein are administered sequentially (e.g., a first optimized influenza HA protein is administered as a priming vaccine followed by administration of a second optimized influenza HA protein as a boosting vaccine), where the first optimized influenza HA protein is different from the second optimized influenza HA protein.

Codon-optimized: As used herein, a "codon-optimized" nucleic acid sequence refers to a nucleic acid sequence that has been altered such that translation of the nucleic acid sequence and expression of the resulting protein is improved optimized for a particular expression system. A "codon-optimized" nucleic acid sequence encodes the same protein as a non-optimized parental sequence upon which the "codon-optimized" nucleic acid sequence is based. For example, a nucleic acid sequence may be "codon-optimized" for expression in mammalian cells (e.g., CHO cells, human cells, mouse cells etc.), bacterial cells (e.g., *E. coli*), insect cells, yeast cells or plant cells.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Determine: Many methodologies described herein include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source. In some embodiments, determining involves comparing one or more features of a sample or entity to a comparable reference.

Epitope: As used herein, the term "epitope" includes any moiety that is specifically recognized by an immunoglobulin (e.g., antibody or receptor) binding component in whole or in part. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: The term "expression", when used in reference to a nucleic acid herein, refers to one or more of the following events: (1) production of an RNA transcript of a DNA template (e.g., by transcription); (2) processing of an RNA transcript (e.g., by splicing, editing, 5' cap formation, and/or 3' end formation); (3) translation of an RNA into a polypeptide; and/or (4) post-translational modification of a polypeptide.

Fusion protein: As used herein, the term "fusion protein" refers to a protein encoded by a nucleic acid sequence engineered from nucleic acid sequences encoding at least a portion of two different (e.g., heterologous) proteins. As persons of skill are no doubt aware, to create a fusion protein nucleic acid sequences are joined such that the resulting reading does not contain an internal stop codon. In some embodiments, fusion proteins as described herein include an influenza HA polypeptide or fragment thereof.

Hemagglutinin (HA) polypeptide: As used herein, the term "hemagglutinin polypeptide" (or "HA polypeptide") refers to one of the three computationally optimized H5N1 HA polypeptide sequences set forth in Table 1.

H5N1 HA polypeptide: An "H5N1 HA polypeptide", as that term is used herein, is an HA polypeptide whose amino acid sequence includes at least one sequence element that is characteristic of H5N1 and distinguishes H5N1 from other HA subtypes. Representative sequence elements can be determined by alignments.

Host: The term "host" is used herein to refer to a system (e.g., a cell, organism, etc.) in which a polypeptide of interest is present. In some embodiments, a host is a system that is susceptible to infection with a particular infectious agent. In some embodiments, a host is a system that expresses a particular polypeptide of interest.

Host cell: As used herein, the phrase "host cell" refers to a cell into which exogenous DNA (recombinant or otherwise) has been introduced. For example, host cells may be used to produce the optimized influenza hemagglutinin polypeptides described herein by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, 5P2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is an administerable composition comprising an immunogen (such as an HA polypeptide). "Immunogenic compositions" include, for example, vaccines. As used herein, "immunize" means to render a subject protected from an infectious disease, such as by vaccination.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza vaccine: As used herein, the term "influenza vaccine" refers to an immunogenic composition capable of stimulating an immune response, administered for the prophylaxis, prevention, amelioration, or treatment of influenza virus infection. An influenza vaccine may include, for example, attenuated or killed influenza virus, subunit preparations thereof (i.e., split-inactivated vaccines), virus-like particles (VLPs) and/or antigenic polypeptides (e.g., the computationally optimized hemagglutinins described herein) or DNA derived from them, or any recombinant versions of such immunogenic materials. Influenza vaccines as described herein may optionally contain one or more adjuvants.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Nucleic acid: As used herein, the phrase "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Optimized influenza HA protein: As used herein, "optimized influenza HA protein," "optimized H5N1 influenza HA polypeptide," or "computationally optimized" refer to a non-naturally occurring HA protein consensus sequence generated by sequence alignments of human and avian H5N1 influenza viruses isolates (as described in, for example, international publications WO2012/036993 and WO2013/122827 to Ross, T. M. et al., which are incorporated by reference herein). Nucleotide sequences encoding optimized HA proteins are further optimized for expression in mammalian cells via codon-optimization and RNA optimization (such as to increase RNA stability). Optimized influenza HA proteins disclosed herein (and set forth herein as SEQ ID NO: 1, SEQ ID NO: 3, and SEQ ID NO: 5) are also referred to as "COBRA" (computationally-optimized broadly reactive antigen) sequences. Optimized HA polypeptides are designed to elicit broadly reactive immune responses in a subject. Their amino acid sequences have been designed by humans and/or their existence and production require action of humans. For example, the computationally optimized HA polypeptides described herein have an amino acid sequence that differs from the amino acid sequences of HA polypeptides found in natural influenza isolates. In the context of the present disclosure, "broadly reactive" means the protein sequence elicits an immune response in a subject that is sufficient to inhibit, neutralize or prevent infection of a broad range of H5N1 influenza viruses (such as most or all influenza viruses within a specific subtype). Co-administration of the optimized H5N1 influenza HA proteins are capable of eliciting an immune response, such as a protective immune response, against most or all H5N1 influenza virus isolates.

Operably linked: As used herein, the phrase "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Outbreak: As used herein, an influenza virus "outbreak" refers to a collection of virus isolates from within a single country in a given year.

Pandemic strain: A "pandemic" influenza strain is one that has caused or has capacity to cause pandemic infection of human populations. In some embodiments, a pandemic strain has caused pandemic infection. In some embodiments, such pandemic infection involves epidemic infection across multiple territories; in some embodiments, pandemic infection involves infection across territories that are separated from one another (e.g., by mountains, bodies of water, as part of distinct continents, etc.) such that infections ordinarily do not pass between them.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions, such as one or more influenza vaccines, and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally. In some embodiments, the term "polypeptide" is used to refer to specific functional classes of polypeptides, such as, HA polypeptides, etc. In some embodiments, a useful polypeptide (e.g., a computationally optimized H5 HA polypeptide as described herein) may comprise or consist of a fragment of a parent polypeptide (e.g., an epitope). In some embodiments, a useful polypeptide as may comprise or consist of multiple (e.g., two, three, four, etc.) fragments (e.g., epitopes), each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. In some embodiments, a useful polypeptide may comprise or consist of multiple (e.g., two, three, four, etc.) fragments (e.g., epitopes), each of which is found in different parent polypeptides than the polypeptide of interest (e.g., fragments that originate in different parent polypeptides, and/or fragments may be present in a different order in the polypeptide of interest than in the parent polypeptides), so that the polypeptide of interest is a derivative of its parent polypeptides.

Prevention: The term "prevention", as used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Recombinant: As used herein, the term "recombinant" is intended to refer to polypeptides (e.g., HA polypeptides as described herein) that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same polypeptide (e.g., two epitopes from two separate H5 HA polypeptides).

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods. Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genet. 6:119-129, 1994. The NCBI Basic Local Alignment Search Tool (BLAST™) (Altschul et al., J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: As used herein, the term "subject" means any mammal, including mice, ferrets and humans. In certain embodiments of the present invention the subject is an adult, an adolescent or an infant. In some embodiments, terms "individual" or "patient" are used and are intended to be interchangeable with "subject". Also contemplated by the present invention are the co-administration of the optimized H5N1 influenza HA proteins and/or performance of the methods to/or birds, including chickens and ducks.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Vaccination: As used herein, the term "vaccination" refers to the administration of a composition (specifically co-administration of two or more of the three computationally optimized H5N1 HA polypeptides described herein) intended to generate an immune response, for example to a disease-causing agent such as influenza. Vaccination can be administered before, during, and/or after exposure to a disease-causing agent, and/or to the development of one or more symptoms, and in some embodiments, before, during, and/or shortly after exposure to the agent. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response. In some embodiments, vaccination includes multiple administrations, appropriately spaced in time, of a vaccinating composition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, influenza VLPs as described herein comprise hemagglutinin (HA) polypeptides and neuraminidase (NA) polypeptides. In some embodiments, influenza VLPs as described herein comprises HA polypeptides, NA polypeptides and/or viral structural polypeptides (e.g., an influenza structural protein such as influenza M1). In some certain embodiments, influenza VLPs as described herein comprises HA polypeptides, NA polypeptides and/or M1 polypeptides. In some embodiments, influenza VLPs as described herein comprises HA polypeptides, NA polypeptides and/or HIV gag polypeptides. As persons of skill are aware, other viral structural proteins may be used as alternatives to those exemplified herein. Influenza VLPs can be produced by transfection of host cells (e.g., mammalian cells) with plasmids encoding HA and NA proteins, and optionally HIV gag proteins. After incubation of the transfected cells for an appropriate time to allow for protein expression (such as for approximately 72 hours), VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. To give but a few examples, influenza VLPs may be analyzed for hemagglutinin activity, dynamic light scattering and hemagglutinin content quantitation by protein staining. Other assays will be readily apparent to persons of skill upon reviewing the present disclosure.

DETAILED DESCRIPTION OF CERTAIN EMBODIMENTS

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Co-Administration of H5N1 Hemagglutinin Computationally Optimized Broadly Reactive Antigens (COBRAs)

Since its re-emergence in late 2004, outbreaks of highly pathogenic avian H5N1 influenza virus have been reported in markets and poultry farms throughout Southeast Asia. An effective vaccine could protect the human population against an emerging, transmissible H5N1 influenza strain. However, one of the challenges to developing effective H5N1 influenza vaccines is the distinct viral lineages that result in antigenic diversity within the subtype. H5N1 viruses are separated into distinct clades based upon phylogenetic distance among the hemagglutinin (HA) genes. There are 10 antigenic clades based upon HA gene sequences. The clades are geographically diverse and are evolving under unique pressures specific to each respective location. Genetic diversity within clade 2 has resulted in distinct subclades and sub-subclades. Despite high levels of HA protein sequence homology between clades (>90%), there is little receptor-blocking antibody cross-reactivity across clades and even within subclades. Developing vaccines that are able to overcome the challenge of H5N1 antigenic diversity by generating cross-clade protective immunity, as disclosed herein, is a crucial step in pandemic preparedness.

In order to overcome these limitations, embodiments disclosed herein rely on a methodology of antigen design using multiple rounds of consensus generation termed computationally optimized broadly reactive antigen (COBRA). This method was designed to address the diversity specifically within clade 2 and utilized global surveillance efforts to generate a vaccine with the potential to elicit increased breadth of antibody responses within this antigenically diverse clade. Provided herein are two second-generation H5N1 COBRA HA antigens that expand the breadth of antibody responses against H5N1 influenza viruses from various clades. Each of the COBRA HA antigens were expressed on virus-like particles (VLPs) and purified as vaccine immunogens. These new versions included addition of avian sequences. One of the vaccines added avian Clade 2 HA sequences to the human Clade 2 sequences of the first generation Human COBRA-2 to yield a Human/Avian Clade 2 COBRA and the second version added avian and human sequences from all clades of H5N1 referred to as All H5N1 COBRA. Both were tested in pre-clinical animal models and compared to wild-type H5N1 HA antigens and our first generation H5N1 COBRA HA vaccine. Each COBRA HA elicited HAI activity against a subset of H5N1 primary viral isolates. However, only when all three vaccines were combined did the elicited antibody response synergistically recognize all 25 viruses from 11 difference clades and subclades of H5N1.

Provided herein is co-administration of H5N1 COBRA HA that expands the breadth of antibody responses in a subject against different H5N1 influenza strains. Co-administration of the present invention includes novel combinations or cocktails of H5N1 COBRA HA proteins, as well as prime-boost administration of H5N1 COBRA HA proteins The compositions described herein comprise combinations or cocktails of optimized hemagglutinin molecules of the H5N1 subtype that do not match naturally occurring strains. In combination, these molecules act synergistically to provide broader coverage to naturally occurring pandemic H5N1 strains than either molecule can provide individually. As noted above, the synergy of the combinations/cocktails described herein is empirically verifiable and is described in the accompanying Examples. Three H5N1 HA computationally optimized antigens (COBRAs) were designed based upon 1) human clade 2 H5N1 sequences, 2) human and avian clade 2 sequences, and 3) all H5N1 influenza sequences recorded between 2005-2008. Each hemagglutinin protein retained the ability to bind the appropriate receptors, as well as the ability to mediate particle fusion, following purification from a mammalian expression system. Separate individual COBRA VLP vaccines were administered to mice and the humoral immune responses were compared to those induced by VLPs containing an HA derived from a primary viral isolate. Using a single vaccination (0.6 ug HA dose with an adjuvant) of the individual COBRAs, all animals vaccinated with COBRA clade 2 HA H5N1 VLPs had protective levels of HAI antibodies to a representative isolate from each subclade of clade 2, but lower titers against other clades. The addition of avian sequences from other clades expanded breadth of HAI antibodies to the divergent clades, but still not all of the 25 H5N1 viruses in the panel were recognized by antibodies elicited any one H5N1 COBRA VLP vaccine. Vaccination of mice with a cocktail of all three COBRA HA VLP vaccines, in a prime-boost regimen, elicited an average HAI titer greater than 1:40 against all 25 viruses. Collectively, the findings demonstrate that the elicited antibody response following VLP vaccination with a combination or cocktail of all three COBRA HA polypeptides synergistically elicits a broadly-reactive set of antibodies that recognized H5N1 viruses from 11 H5N1 clades/subclades isolated over a 12 year span.

The amino acid sequences of the particular optimized influenza HA polypeptides utilized in embodiments of the invention are set forth herein as SEQ ID NO: 1 (All H5 COBRA), SEQ ID NO: 3 (Human-Avian COBRA-2), and SEQ ID NO: 5 (Human COBRA-2). The cocktails described herein comprise various combinations of computationally optimized hemagglutinin antigens selected from the group consisting of sequences set forth in Table 1.

TABLE 1

| | |
|---|---|
| All H5N1 COBRA | MEKIVLLLAIVSLVKSDQICIGYHANNSTEQVDTIMEKNVT VTHAQDILEKTHNGKLCDLDGVKPLILRDCSVAGWLLGNPM CDEFINVPEWSYIVEKASPANDLCYPGDFNDYEELKHLLSR INHFEKIQIIPKSSWSNHEASSGVSSACPYQGKSSFFRNVV WLIKKNSAYPTIKRSYNNTNQEDLLVLWGIHHPNDAAEQTK |

TABLE 1-continued

```
                LYQNPTTYISVGTSTLNQRLVPKIATRSKVNGQSGRMEFFW
                TILKPNDAINFESNGNFIAPEYAYKIVKKGDSAIMKSELEY
                GNCNTKCQTPMGAINSSMPFHNIHPLTIGECPKYVKSNRLV
                LATGLRNSPQRERRRKKRGLFGAIAGFIEGGWQGMVDGWYG
                YHHSNEQGSGYAADKESTQKAIDGVTNKVNSIIDKMNTQFE
                AVGREFNNLERRIENLNKKMEDGFLDVWTYNAELLVLMENE
                RTLDFHDSNVKNLYDKVRLQLRDNAKELGNGCFEFYHKCDN
                ECMESVRNGTYDYPQYSEEARLKREEISGVKLESIGTYQIL
                SIYSTVASSLALAIMVAGLSLWMCSNGSLQCRICI
                (SEQ ID NO: 1)

Human/Avian COBRA-2   MEKIVLLLAIVSLVKSDQICIGYHANNSTEQVDTIMEKNVT
                VTHAQDILEKTHNGKLCDLDGVKPLILRDCSVAGWLLGNPM
                CDEFINVPEWSYIVEKANPANDLCYPGNFNDYEELKHLLSR
                INHFEKIQIIPKSSWSDHEASSGVSSACPYQGKSSFFRNVV
                WLIKKNSAYPTIKRSYNNTNQEDLLVLWGIHHPNDAAEQTR
                LYQNPTTYISVGTSTLNQRLVPKIATRSKVNGQSGRMEFFW
                TILKPNDAINFESNGNFIAPEYAYKIVKKGDSAIMKSELEY
                GNCNTKCQTPMGAINSSMPFHNIHPLTIGECPKYVKSNRLV
                LATGLRNSPQRERRRKRGLFGAIAGFIEGGWQGMVDGWYGY
                HHSNEQGSGYAADKESTQKAIDGVTNKVNSIIDKMNTQFEA
                VGREFNNLERRIENLNKKMEDGFLDVWTYNAELLVLMENER
                TLDFHDSNVKNLYDKVRLQLRDNAKELGNGCFEFYHKCDNE
                CMESVRNGTYDYPQYSEEARLKREEISGVKLESIGTYQILS
                IYSTVASSLALAIMVAGLSLWMCSNGSLQCRICI
                (SEQ ID NO: 3)

Human COBRA-2   MEKIVLLLAIVSLVKSDQICIGYHANNSTEQVDTIMEKNVT
                VTHAQDILEKTHNGKLCDLDGVKPLILRDCSVAGWLLGNPM
                CDEFINVPEWSYIVEKANPANDLCYPGNFNDYEELKHLLSR
                INHFEKIQIIPKSSWSDHEASSGVSSACPYQGSPSFFRNVV
                WLIKKNNTYPTIKRSYNNTNQEDLLVLWGIHHPNDAAEQTR
                LYQNPTTYISVGTSTLNQRLVPKIATRSKVNGQSGRMEFFW
                TILKPNDAINFESNGNFIAPEYAYKIVKKGDSAIMKSELEY
                GNCNTKCQTPIGAINSSMPFHNIHPLTIGECPKYVKSNRLV
                LATGLRNSPQRESRRKKRGLFGAIAGFIEGGWQGMVDGWYG
                YHHSNEQGSGYAADKESTQKAIDGVTNKVNSIIDKMNTQFE
                AVGREFNNLERRIENLNKKMEDGFLDVWTYNAELLVLMENE
                RTLDFHDSNVKNLYDKVRLQLRDNAKELGNGCFEFYHKCDN
                ECMESVRNGTYDYPQYSEEARLKREEISGVKLESIGTYQIL
                SIYSTVASSLALAIMVAGLSLWMCSNGSLQCRICI
                (SEQ ID NO: 5)
```

Particularities concerning the design and production of these molecules have been described previously, particularly in International Publications WO2012/036993 and WO2013/122827, which are incorporated herein by reference in their entirety. The optimized HA polypeptides were developed through a series of HA protein alignments, and subsequent generation of consensus sequences based on thousands of human and avian H5N1 influenza isolates.

Further provided are isolated nucleic acid molecules encoding a recombinant, optimized influenza HA polypeptide disclosed herein. In some embodiments, the nucleic acid molecule is codon-optimized for expression in mammalian cells. The nucleic acid molecule is optionally further optimized for RNA stability. Three exemplary codon-optimized HA nucleic acid sequences are set forth in Table 2 as SEQ ID NO: 2, SEQ ID NO: 4, and SEQ ID NO: 6.

TABLE 2

```
                         All H5N1 COBRA
atggaaaaga tcgtgctgct gctggccatc gtgtccctgg tgaagagcga ccagatttgc   60
atggctacc  acgccaacaa tagcacagag caggtggaca ccatcatgga gaaaaacgtg  120
accgtgaccc acgcccagga catcctggag aaaacccaca acggcaagct gtgtgacctg  180
gacggcgtga agcccctgat cctgagagac tgctccgtgg ccggctggct gctgggcaac  240
cccatgtgtg acgagttcat caacgtgccc gagtggagct acatcgtgga aaggccagc   300
cccgccaacg acctgtgcta ccccggcgac ttcaacgact acgaggagct gaagcacctg  360
ctgtcccgga tcaaccactt cgagaagatc cagatcatcc ccaagagcag ctggagcaac  420
cacgaggcca gcagcggcgt gtccagcgcc tgcccctacc agggcaagag cagcttcttc  480
cggaacgtgg tctggctgat caagaagaac tctgcctatc ccaccatcaa gcggagctac  540
aacaacacca ccaggagga tctgctggtc ctgtggggca tccaccaccc caacgacgcc  600
gccgagcaga ccaagctgta ccagaacccc accacctaca tcagcgtggg caccagcacc  660
ctgaaccagc ggctggtgcc caagatcgcc accggtcca aagtgaacgg ccagagcggc  720
cggatggaat tcttctggac catcctgaag cccaacgatg ccatcaactt cgagagcaac  780
ggcaacttca tcgcccccga gtacgcctac aagatcgtga agaagggcga cagcgccatc  840
atgaagagcg agctgtacgg caactgc aacaccaagt gccagacccc catgggcgc   900
atcaacagca gcatgccctt ccacaacatc caccccctga ccatcggcga gtgccccaag  960
tacgtgaaga gcaacaggct ggtgctggcc accggcctgc ggaacagccc cagcgggag  1020
cggcggagga agaagcgggg cctgttcggc gccatcgccg gcttcatcga gggcggctgg 1080
cagggcatgg tggacgggtg gtacggctac caccacagca tgagcaggg cagcggctac 1140
gccgccgaca agagagcac ccagaaggcc atcgacggcg tcaccaacaa ggtgaacagc 1200
```

TABLE 2-continued

```
atcatcgaca agatgaacac ccagttcgag gccgtgggcc gggagttcaa caacctggaa   1260
cggcggatcg agaacctgaa caagaaaatg gaagatggct tcctggacgt gtggacctac   1320
aacgccgaac tcctggtgct gatggaaaac gagcggaccc tggacttcca cgacagcaac   1380
gtgaagaacc tgtacgacaa agtgcggctg cagctgcggg acaacgccaa agagctgggc   1440
aacggctgct tcgagttcta ccacaagtgc gacaacgagt gcatggaaag cgtgcggaac   1500
ggcacctacg actaccccca gtacagcgag gaagcccggc tgaagcggga ggaaatcagc   1560
ggcgtgaaac tggaaagcat cggcacctac cagatcctga gcatctacag caccgtggcc   1620
agcagcctcg ctctggccat tatggtggcc ggcctgagcc tgtggatgtg cagcaacggc   1680
agcctgcagt gccggatcgg atccagatct gctagcgtcg actctagatt aattaa      1736
(SEQ ID NO: 2)
```

Human/Avian COBRA-2

```
atggagaaga tcgtgctgct gctggccatc gtgtccctgg tgaagagcga ccagatttgc     60
atcggctacc acgccaacaa tagcaccgag caagtggaca ccatcatgga gaaaaacgtg    120
accgtgaccc acgctcagga catcctcgaa aaacccaca acggcaagct gtgcgatctg     180
gacggcgtga agccctgat cctgagagac tgcagcgtgg ccggctggct gctgggcaat     240
cccatgtgcg acgagttcat caacgtgccc gagtggagct acatcgtgga gaaggccaac    300
cccgccaacg acctgtgcta ccccggcaac ttcaacgact acgaggagct gaagcacctg    360
ctgagccgga tcaaccactt cgagaagatc cagatcatcc caagagcag ctggagcgac     420
catgaggcaa gcagcggcgt gtccagcgcc tgccctacc agggcaagtc cagcttcttc     480
cgcaacgttg tgtggctgat caagaagaac agcgcctacc ccaccatcaa gcggagctac    540
aacaacacca accaggagga cctgctggtc ctgtggggca tccaccaccc caacgacgcc    600
gccgagcaga cccggctgta ccagaacccc accacctaca tctctgtggg caccagcacc    660
ctgaaccagc ggctggtgcc caagatcgcc acccggagca aggtgaacgg ccagagcggc    720
cggatggagt tcttctggac catcctgaag cccaacgatg ccatcaactt cgagagcaac    780
ggcaacttca tcgcccccga gtacgcctac aagatcgtga agaagggcga cagcgccatc    840
atgaagtccg agctggagta cggcaactgt aacaccaagt gccagacccc catgggcgcc    900
atcaacagca gcatgccctt ccacaacatc caccccctga ccatcggcga gtgccccaag    960
tacgtgaaga gcaacaggct ggtgctggcc accggcctga aaacagccc ccagagagag    1020
cggagaagaa agagaggcct gttcggcgcc attgccggct catcgaggg cggctggcag    1080
ggcatggtgg acgggtggta cggctaccac cactccaacg agcagggcag cggctacgcc    1140
gccgacaaag agagcaccca gaaagctatc gacgcgtga ccaacaaagt gaacagcatc     1200
atcgacaaga tgaataccca gttcgaggcc gtgggcagag agttcaacaa cctggaaaga    1260
agaatcgaga acctgaacaa gaaaatggaa gatggctttc tggatgtgtg gacctacaac    1320
gccgagctgc tggtgctgat ggaaaacgag cggaccctgg acttccacga cagcaacgtg    1380
aagaatctgt acgacaaagt gcggctgcag ctgagagaca cgccaaaga gctgggcaac     1440
ggctgcttcg agttctacca caagtgcgac aatgagtgca tggaaagcgt gcggaacggc    1500
acctacgact accccagta cagcgaggaa gcccggctga agagagaaga gatttccggc    1560
gtgaagctga aaagcatcgg cacctaccag atcctgagca tctacagcac cgtggccagc    1620
agcctggccc tggccatcat ggtggccggc ctgagcctgt ggatgtgcag caacggcagc    1680
ctgcagtgcc ggatctgcat cggatccaga tctgctagcg tcgactctag attaattaa    1739
(SEQ ID NO: 4)
```

Human COBRA-2

```
atg gaa aag atc gtg ctg ctg ctg gct atc gtg agc ctg gtg aag agc       48
gac cag att tgc atc ggc tac cac gcc aac aac agc acc gag cag gtg       96
gac acc atc atg gaa aag aac gtc acc gtg acc cac gcc cag gac atc      144
ctg gaa aag acc cac aac ggc aag ctg tgc gac ctg gac gtg aag          192
ccc ctg atc ctg agg gac tgc agc gtg gcc ggc tgg ctg ctg ggc aac      240
ccc atg tgc gac gag ttc atc aac gtg ccc gag tgg agc tac atc gtg      288
gag aag gcc aac ccc gcc aac gac ctg tgc tac ccc ggc aac ttc aac      336
gac tac gag gaa ctg aag cac ctg ctg tcc agg atc aac cac ttc gag      384
aag atc cag atc atc ccc aag agc agc tgg tcc gac cac gag gcc agc      432
agc ggc gtg agc agc gcc tgc cca tac cag ggc agc ccc agc ttc ttc      480
aga aac gtg gtg tgg ctg atc aag aag aac aac acc tac ccc acc atc      528
aag agg tcc tac aac aac acc aac cag gaa gat ctg ctg gtc ctg tgg      576
ggc atc cac cac cct aat gac gcc gcc gaa cag acc agg ctg tac cag      624
aac ccc acc acc tac atc agc gtg ggc aca agc acc ctg aac cag agg      672
ctg gtg ccc aag atc gcc acc agg tcc aag gtg aac gga cag tcc ggc      720
agg atg gaa ttc ttc tgg acc atc ctg aag cct aac gac gcc atc aac      768
ttc gag agc aac ggc aac ttt atc gcc ccc gag tac gcc tac aag atc      816
gtg aag aag ggc gac agc gcc atc atg aag agc gag ctg gaa tac ggc      864
aac tgc aac acc aag tgc cag acc ccc atc ggc gcc atc aac agc agc      912
atg ccc ttc cac aac atc cac ccc ctg acc atc ggc gag tgc ccc aag      960
tac gtg aag agc aac agg ctg gtg ctg gcc acc ggc ctg agg aac agc     1008
ccc cag aga gag agc aga aga aag aag agg ggc ctg ttc ggc gct atc     1056
gcc ggc ttc atc gag ggc ggc tgg cag ggc atg gtg gac ggg tgg tac     1104
ggc tac cac cac tct aac gag cag ggc agc ggc tac gcc gcc gac aaa     1152
gag agc acc cag aag gcc atc gac ggc gtc acc aac aag gtg aac agc     1200
atc atc gac aag atg aac acc cag ttc gag gcc gtg ggc aga gag ttc     1248
aac aac ctg gaa agg cgg atc gag aac ctg aac aag aaa atg gaa gat     1296
ggc ttc ctg gac gtg tgg acc tac aac gcc gag ctg ctg gtg ctg atg     1344
gaa aac gag agg acc ctg gac ttc cac gac agc aac gtg aag aac ctg     1392
tac gac aaa gtg cgg ctg cag ctg agg gac aac gcc aaa gag ctg ggc     1440
aac ggc tgc ttc gag ttc tac cac aag tgc gac aac gag tgc atg gaa     1488
agc gtg agg aac ggc acc tac gac tac ccc cag tac agc gag gaa gcc     1536
agg ctg aag agg gaa gag atc agc gga gtg aag ctg gaa agc atc ggc     1584
acc tac cag atc ctg agc atc tac agc acc gtc gcc agc agc ctg gcc     1632
```

TABLE 2-continued

```
ctg gct atc atg gtg gcc gga ctg agc ctg tgg atg tgc agc aac ggc    1680
agc ctg cag tgc agg atc tgc atc tga                                1707
(SEQ ID NO: 6)
```

SEQ ID NO: 2 is a codon-optimized nucleic acid sequence encoding the H5N1 influenza COBRA HA of SEQ ID NO: 1. SEQ ID NO: 4 is a codon-optimized nucleic acid sequence encoding the H5N1 influenza COBRA HA of SEQ ID NO: 3. SEQ ID NO: 6 is a codon-optimized nucleic acid sequence encoding the H5N1 influenza COBRA HA of SEQ ID NO: 5. Provided herein are isolated nucleic acid molecules comprising a nucleotide sequence encoding an optimized influenza HA polypeptide, wherein the nucleotide sequence encoding the optimized influenza HA polypeptide is at least 90%, at least 94%, at least 95%, at least 96%, at least 97%, at least 98% or at least 99% identical to SEQ ID NOS: 1, 3 or 5. In some embodiments, the sequence of the nucleic acid molecule encoding the optimized influenza HA polypeptide is at least 90%, at least 94%, at least 95%, at least 96%, at least 97%, at least 98% or at least 99% identical to nucleotides of 4-1698 of SEQ ID NO: 2, nucleotides 4-1701 of SEQ ID NO: 4, or nucleotides 4-1707 of SEQ ID NO: 6. In particular examples, the sequence of the nucleic acid molecule encoding the optimized influenza HA polypeptide comprises or consists of nucleotides of 4-1698 of SEQ ID NO: 2, nucleotides 4-1701 of SEQ ID NO: 4 or nucleotides 4-1707 of SEQ ID NO: 6. In other embodiments, the sequence of the nucleic acid molecule encoding the optimized influenza HA polypeptide is at least 90%, at least 94%, at least 95%, at least 96%, at least 97%, at least 98% or at least 99% identical to nucleotides of 1-1698 of SEQ ID NO: 2, nucleotides 1-1701 of SEQ ID NO: 4, or nucleotides 1-1707 of SEQ ID NO: 6. In particular examples, the sequence of the nucleic acid molecule encoding the optimized influenza HA polypeptide comprises or consists of nucleotides 1-1698 of SEQ ID NO: 2, nucleotides 1-1701 of SEQ ID NO: 4, or nucleotides 1-1707 of SEQ ID NO: 6. Optimized influenza HA polypeptides encoded by the nucleic acid molecules, vectors comprising the nucleic acid molecules, and host cells containing the disclosed vectors are also provided herein.

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS, 293 or CHO cell). Host cells transformed with an expression vector are grown under conditions permitting production of an optimized HA polypeptide the present invention followed by recovery of an optimized HA polypeptide.

Vectors comprising the nucleic acid molecules encoding recombinant, optimized influenza HA polypeptides are also provided by the present disclosure. The vector can be any suitable vector for expression of the HA polypeptide, such as a mammalian expression vector. In particular examples, the vector is the pTR600 expression vector (U.S. Patent Application Publication No. 2002/0106798, herein incorporated by reference; Ross et ah, Nat Immunol. 1(2): 102-103, 2000; Green et al., Vaccine 20:242-248, 2001). In some examples, the vector includes a promoter operably linked to the nucleic acid sequence encoding the optimized influenza HA polypeptide. In particular examples, the promoter is a CMV promoter.

Fusion proteins comprising one or more of the optimized influenza HA polypeptides as described herein (e.g., an HA polypeptide that appears in Table 1) are further provided by the present disclosure.

Provided herein are compositions (i.e., cocktails) comprising combinations of non-naturally occurring recombinant H5N1 influenza HA polypeptides having an optimized amino acid sequence for eliciting a broadly reactive immune response against H5N1 influenza. In some embodiments, the compositions described herein comprise (i) a first optimized influenza HA polypeptide comprising an amino acid sequence at least 99.8% identical to SEQ ID NO: 1, and (ii) second optimized influenza HA polypeptide comprising an amino sequence at least 99.6% identical to SEQ ID NO: 3. In particular embodiments, the amino acid sequence of the first optimized influenza HA polypeptide that is at least 99.8% identical to SEQ ID NO: 1 lacks the N-terminal methionine residue. In particular embodiments, the amino acid sequence of the second optimized influenza HA polypeptide that is at least 99.6% identical to SEQ ID NO: 3 lacks the N-terminal methionine residue. In some embodiments, the cocktails comprise a first optimized influenza HA polypeptide comprising an amino acid sequence at least 99.8% identical to residues 2-566 of SEQ ID NO: 1 and a second optimized influenza HA polypeptide comprising an amino acid sequence at least 99.6% identical to residues 2-567 of SEQ ID NO: 3. In particular examples, the amino acid sequences of the first and second optimized influenza HA polypeptides comprise or consists of the amino acid sequence of residues 2-566 of SEQ ID NO: 1 and residues 2-567 of SEQ ID NO: 3. In some embodiments, the cocktails comprise a first optimized influenza HA polypeptide comprising an amino acid sequence at least 99.8% identical to residues 2-566 of SEQ ID NO: 1 and a second optimized influenza HA polypeptide comprising an amino acid sequence at least 99.6% identical to residues 2-567 of SEQ ID NO: 3. In some embodiments, the amino acid sequences of the optimized influenza HA polypeptides in the composition are at least 95%, at least 96%, at least 97%, at least 98%, at least 99% identical to SEQ ID NO: 1, SEQ ID NO: 3, residues 2-566 of SEQ ID NO: 1 or residues 2-567 of SEQ ID NO: 3. In some embodiments, the amino acid sequences of the optimized influenza HA polypeptides in the composition are 100% homologous to SEQ ID NO: 1, SEQ ID NO: 3, residues 2-566 of SEQ ID NO: 1 or residues 2-567 of SEQ ID NO: 3. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 3.

In some embodiments, the compositions described herein comprise (i) a first optimized influenza HA polypeptide comprising an amino acid sequence at least 99.8% identical to SEQ ID NO: 1, and (ii) second optimized influenza HA polypeptide comprising an amino sequence at least 99% identical to SEQ ID NO: 5. In particular embodiments, the amino acid sequence of the first optimized influenza HA polypeptide that is at least 99.8% identical to SEQ ID NO: 1 lacks the N-terminal methionine residue. In particular embodiments, the amino acid sequence of the second optimized influenza HA polypeptide that is at least 99% identical to SEQ ID NO: 5 lacks the N-terminal methionine residue. In particular embodiments, the amino acid sequence of the first optimized influenza HA polypeptide is at least 99.8% identical to residues 2-566 of SEQ ID NO: 1. In particular embodiments, the amino acid sequence of the second optimized influenza HA polypeptide is at least 99% identical to residues 2-568 of SEQ ID NO: 5. In particular embodiments, the amino acid sequence of the first optimized influenza HA polypeptide comprises or consists of residues 2-566 of SEQ ID NO: 1. In particular embodiments, the amino acid sequence of the second optimized influenza HA polypeptide comprises or consists of residues 2-568 of SEQ ID NO: 5. In some embodiments, the amino acid sequences of the optimized influenza HA polypeptides in the composition are at least 95%, at least 96%, at least 97%, at least 98%, at least 99% identical to SEQ ID NO: 1, SEQ ID NO: 5, residues 2-566 of SEQ ID NO: 1 or residues 2-568 of SEQ ID NO: 5. In some embodiments, the amino acid sequences of the optimized influenza HA polypeptides in the composition are 100% homologous to SEQ ID NO: 1, SEQ ID NO: 5, residues 2-566 of SEQ ID NO: 1 or residues 2-568 of SEQ ID NO: 5. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 5.

In some embodiments, the compositions described herein comprise (i) a first optimized influenza HA polypeptide comprising an amino acid sequence at least 99.6% identical to SEQ ID NO: 3, and (ii) second optimized influenza HA polypeptide comprising an amino sequence at least 99% identical to SEQ ID NO: 5. In particular embodiments, the amino acid sequence of the first optimized influenza HA polypeptide that is at least 99.6% identical to SEQ ID NO: 3 lacks the N-terminal methionine residue. In particular embodiments, the amino acid sequence of the second optimized influenza HA polypeptide that is at least 99% identical to SEQ ID NO: 5 lacks the N-terminal methionine residue. In particular embodiments, the amino acid sequence of the first optimized influenza HA polypeptide is at least 99.6% identical to residues 2-567 of SEQ ID NO: 3. In particular embodiments, the amino acid sequence of the second optimized influenza HA polypeptide is at least 99% identical to residues 2-568 of SEQ ID NO: 5. In particular embodiments, the amino acid sequence of the first optimized influenza HA polypeptide comprises or consists of residues 2-567 of SEQ ID NO: 3. In particular embodiments, the amino acid sequence of the second optimized influenza HA polypeptide comprises or consists of residues 2-568 of SEQ ID NO: 5. In some embodiments, the amino acid sequences of the optimized influenza HA polypeptides in the composition are at least 95%, at least 96%, at least 97%, at least 98%, at least 99% identical to SEQ ID NO: 3, SEQ ID NO: 5, residues 2-567 of SEQ ID NO: 3 or residues 2-568 of SEQ ID NO: 5. In some embodiments, the amino acid sequences of the optimized influenza HA polypeptides in the composition are 100% homologous to SEQ ID NO: 3, SEQ ID NO: 5, residues 2-567 of SEQ ID NO: 3 or residues 2-568 of SEQ ID NO: 5. In some embodiments, the compositions comprise at least two different optimized influenza HA polypeptides, wherein the amino acid sequence of the polypeptides comprises no more than two, or no more than one substitution relative to SEQ ID NO: 3 or SEQ ID NO: 5.

In some embodiments, the compositions described herein comprise (i) a first optimized influenza HA polypeptide comprising an amino acid sequence at least 99.8% identical to SEQ ID NO: 1, a (ii) second optimized influenza HA polypeptide comprising an amino sequence at least 99.6% identical to SEQ ID NO: 3, and (iii) a third optimized influenza HA polypeptide comprising an amino acid sequence at least 99% identical to SEQ ID NO: 5. In particular embodiments, the amino acid sequence of the first optimized influenza HA polypeptide that is at least 99.8% identical to SEQ ID NO: 1 lacks the N-terminal methionine residue. In particular embodiments, the amino sequence of the second optimized influenza HA polypeptide that is at least 99.6% identical to SEQ ID NO: 3 lacks the N-terminal methionine residue. In particular embodiments, the amino acid sequence of the third optimized influenza HA polypeptide that is at least 99% identical to SEQ ID NO: 5 lacks the N-terminal methionine residue. In particular embodiments, the amino acid sequence of the first optimized influenza HA polypeptide is at least 99.8% identical to residues 2-566 of SEQ ID NO: 1. In particular embodiments, the amino acid sequence of the second optimized influenza HA polypeptide is at least 99.6% identical to residues 2-567 of SEQ ID NO: 5. In particular embodiments, the amino acid sequence of the third optimized influenza HA polypeptide is at least 99% identical to amino acids 2-568 of SEQ ID NO: 5. In some embodiments, the amino acid sequences of the optimized influenza HA polypeptides in the composition are at least 95%, at least 96%, at least 97%, at least 98%, or at least 99% identical to SEQ ID NO: 1 and SEQ ID NO: 3 and SEQ ID NO: 5; or at least 95%, at least 96%, at least 97%, at least 98%, or at least 99% identical to residues 2-566 of SEQ ID NO: 1 and residues 2-567 of SEQ ID NO: 3 and residues 2-568 of SEQ ID NO: 5. In some embodiments, the amino acid sequences of the optimized influenza HA polypeptides in the composition are 100% homologous to SEQ ID NO: 1 and SEQ ID NO: 3 and SEQ ID NO: 5, or residues 2-566 of SEQ ID NO: 1 and residues 2-567 of SEQ ID NO: 3 and residues 2-568 of SEQ ID NO: 5. In some embodiments, the compositions comprise at least three different optimized influenza HA polypeptides, wherein the amino acid sequences of the polypeptides comprises no more than three, no more than two, or no more than one substitution relative to SEQ ID NO: 1, SEQ ID NO: 3, or SEQ ID NO: 5.

The optimized HA polypeptides may be expressed/produced in diverse eukaryotic-based expression systems, including microalgae (e.g. *Schizochytrium* sp.; see, e.g., Bayne, A-C. V. et al., *PLOS ONE,* 8(4):e61790, April 2013), plant-based systems (e.g., tobacco plants; see, e.g., Jul-Larsen, A., et al., *Hum Vaccin Immunother.,* 8(5):653-61, 2012), yeast (see, e.g., Athmaram, T. N. et al., *Virol J.,* 8:524, 2011), and fungi (see, e.g., Allgaier, S. et al., *Biologicals,* 37:128-32, 2009). Bacterial based expression systems are also encompassed by the present invention (see, e.g., Davis, A. R. et al., Gene, 21:273-284, 1983). These publications are incorporated herein by reference in their entirety.

Computationally optimized HA polypeptides of the present invention may be purified by any technique known in the art, including conventional ion exchange chromatography, hydrophobic interaction chromatography, reverse phase chromatography and/or gel filtration. Computationally optimized HA polypeptides of the present invention may also be recovered from conditioned media following secretion from eukaryotic or prokaryotic cells.

Influenza Virus-Like Particles (VLPs)

In some embodiments, the present invention provides for influenza virus-like particles (VLPs) and combinations thereof comprising one or more of the computationally optimized H5N1 influenza HA polypeptides (or immunogenic fragment thereof) as described herein (e.g., an HA polypeptide that appears in Table 1). The influenza VLPs are, in some embodiments, generally made up of HA, NA and virus structural (e.g., HIV gag) proteins. Production of influenza VLPs is known in the art and will be readily apparent to persons of skill upon reading the present disclosure. For example, influenza VLPs may be produced by transfection of host cells with plasmids encoding the HA, NA and HIV gag proteins. To give but one example, a suitable host cell includes a human cell (e.g., HEK293T). After incubation of the transfected cells for an appropriate time to allow for protein expression (such as for approximately 72 hours), VLPs may be isolated from cell culture supernatants. In some embodiments, influenza VLPs as disclosed herein may be used as influenza vaccines to elicit a broadly neutralizing immune response against H5N1 influenza viruses.

Whole Influenza Viruses

Also provided are whole recombinant influenza viruses comprising one or more of the computationally optimized recombinant HA polypeptides (or immunogenic fragment or fragments thereof) described herein. The recombinant influenza viruses can be produced by plasmid-based reverse genetics (see, e.g., Neumann, G. et la., *Reverse Genetics of Influenza Viruses, Methods Mol Biol.*, 2012, 865:193-206; incorporated by reference herein) and egg-based technologies; e.g. a recombinant virus comprising a computationally optimized H5 HA polypeptide as described herein, a wild-type NA polypeptide from an H5N1 influenza strain and a backbone of internal protein genes from a donor virus (e.g., influenza A/Puerto Rico/8/34 (PR8)) that confers a high yield in eggs. For example, six plasmids encoding the internal proteins of the high-growth influenza A/Puerto Rico/8/34 (PR8) donor virus can be co-transfected with two plasmids encoding a computationally optimized H5N1 HA polypeptide as described herein and a wild-type neuraminidase (NA) glycoprotein into qualified mammalian cells (e.g., Vero cells), followed by isolation of the recombinant virus. Recombinant viruses containing internal protein genes from the PR8 virus may be used to prepare live-attenuated and/or inactivated influenza virus vaccines (see, e.g., Fodor, E. et al. *Rescue of influenza A virus from Recombinant DNA. J. Virol.*, 1999, 73, 9679-9682; incorporated by reference herein).

It is possible to incorporate the computationally optimized H5N1 HA polypeptide as described herein into a live, attenuated influenza virus. Live, attenuated viruses can elicit a long-lasting and broad immune (humoral and cellular) response that represents a naturally occurring transient infection, particularly, in younger subjects whose immune system are not as fully developed. For example, a live attenuated influenza vaccines can be produced using NA genes from circulating viruses and computationally optimized H5N1 HA sequences on an attenuated, temperature-sensitive, cold adapted virus backbone (e.g., a 6:2 reassortant with six internal gene segments from an attenuated donor virus such as A/Ann Arbor/6/60 that confers temperature-sensistive and cold-adapted phenotypes and is attenuated for virulence). This backbone prevents replication at temperatures above a certain temperature (e.g., 33° C.), thereby restricting replication to the upper but not lower respiratory tract. Methods of making and using such live, attenuated, temperature sensitive (aka cold adapted) influenza viruses are well known in the art. See e.g., He et al., *Molecular Basis of Live-Attenuated Influenza Virus*, PloS One., 2013, 8(3):e60413; Sridhar et al., *Influenza Vaccination Strategies: Comparing Inactivated and Live Attenuated Influenza Vaccines,* 2015, Vaccines, 2015, 3(2):373-89.

Distinct recombinant influenza viruses, each comprising a different recombinant, optimized HA polypeptide disclosed herein, can be separately produced and then combined into the combinations/cocktails. The recombinant influenza virus combinations/cocktails can be used as influenza vaccines to elicit a protective immune response against human and avian H5N1 influenza viruses; for example, they can be administered as components of a live-attenuated or split-inactivated vaccine.

Thus, in some embodiments, the present invention provides inactivated H5N1 influenza vaccines comprising combinations or cocktails of the computationally optimized H5N1 influenza HA polypeptides (or immunogenic fragments thereof) as described herein (e.g., cocktails of the HA polypeptides that appear in Table 1), wherein the vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In some embodiments, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., 1998, *Textbook of Influenza*, Blackwell Science, Malden, Mass.; incorporated herein by reference). To assess the potency of the vaccine, the single radial immunodiffusion (SRD) test can be used (Schild et al., 1975, *Bull. World Health Organ.*, 52:43-50 & 223-31; Mostow et al., 1975, *J. Clin. Microbiol.*, 2:531; both of which are incorporated herein by reference).

In some embodiments, influenza virus for use in vaccines is grown in eggs, for example, in embryonated hen eggs, in which case the harvested material is allantoic fluid. Alternatively or additionally, influenza virus or optimized hemagglutinin polypeptides may be produced from any method using tissue culture to grow the virus. Suitable cell substrates for growing the virus or otherwise recombinantly producing the optimized hemagglutinin polypeptides include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Immunogenic Compositions

Also provided herein are immunogenic compositions (e.g., vaccines) comprising combinations or cocktails of the computationally optimized H5N1 influenza HA polypeptides (or immunogenic fragment thereof) as described herein (e.g., cocktails of the HA polypeptides that appear in Table 1), or a fusion protein or VLP or split or inactive virus comprising the optimized influenza HA proteins. In some embodiments, the compositions further comprise a pharmaceutically acceptable carrier.

In some embodiments, vaccines in accordance with the invention further comprise one or more adjuvants. For example, alum, aluminum salts (Baylor et al., 2002, *Vaccine*, 20:S18; incorporated herein by reference) and monophosphoryl lipid A (MPL; Ribi et al., 1986, *Immunology and Immunopharmacology of Bacterial Endotoxins*, Plenum Publ. Corp., NY, p. 407; incorporated herein by reference) can be used as adjuvants in human vaccines. Alternatively or additionally, new compounds are currently being tested as adjuvants in human vaccines, such as MF59 (See, e.g., Ott et al., "MF59—*Design and Evaluation of a Safe and Potent Adjuvant for Human Vaccines*" in Vaccine Design: *The Subunit and Adjuvant Approach* (Powell, M. F. and Newman, M. J. eds.) Plenum Press, New York, 1995, pp. 277-296; incorporated herein by reference); CpG oligodeoxynudeotide (ODN) adjuvants such as CPG 7909 (Cooper et al., 2004, Vaccine, 22:3136; incorporated herein by reference); Monophosphoryl lipid A (MPL) adjuvants and lipid A mimetis including AS04 (Didierlaurent, A. M. et al, *J. Immunol.*, 2009, 183: 6186-6197; incorporated by reference herein), monophosphoryl lipid A (MPL, GSK) and glucopyranosyl lipid A GLA (Immune Design Corporation, IDC); AF03 (Klucker, M. F. et al, *J. Pharm Sci.*, 2012, 101: 4490-4500; incorporated herein by reference); the TLR-3 ligand polyinosinic:polycytidylic acid [poly(I:C)]; TLR9 adjuvants such as IC31 (Riedl, K. et al., *Vaccine*, 2008, 26: 3461-3468; incorporated herein by reference); imidazoquinolines (double cyclic organic molecules that act as TLR-7/8 agonists) such as imiquimod (R837) or resiquimod (R848); saponins such as QS21 (Ghochikyan et al., 2006, Vaccine, 24:2275; incorporated herein by reference), ISCOMATRIX adjuvant (Duewell, P., et al., *J. Immunol*, 2011, 187: 55-63; incorporated herein by reference), and Matrix-M™ (Novavax).

Additionally, some adjuvants are known in the art to enhance the immunogenicity of influenza vaccines, such as poly[di(carboxylatophenoxy)phosphazene] (PCCP; Payne et al., 1998, *Vaccine*, 16:92; incorporated herein by reference), interferon-γ (Cao et al., 1992, *Vaccine*, 10:238; incorporated herein by reference), block copolymer P1205 (CRL1005; Katz et al., 2000, *Vaccine*, 18:2177; incorporated herein by reference), interleukin-2 (IL-2; Mbwuike et al., 1990, *Vaccine*, 8:347; incorporated herein by reference), and polymethyl methacrylate (PMMA; Kreuter et al., 1981, *J. Pharm. Sci.*, 70:367; incorporated herein by reference).

In general, the immunogenic compositions will include one or more inactive agents such as a sterile, biocompatible carrier including, but not limited to, sterile water, saline, buffered saline, or dextrose solution. Alternatively or additionally, the composition can contain any of a variety of additives, such as stabilizers, buffers, excipients (e.g., sugars, amino acids, etc.), or preservatives. Pharmaceutically acceptable carriers used in particular embodiments include, but are not limited to, saline, buffered saline, dextrose, water, glycerol, ethanol, and combinations thereof. In some embodiments, the carrier and composition are sterile, and the formulation suits the mode of administration. In some embodiments, an immunogenic composition contains minor amounts of wetting or emulsifying agents, or pH buffering agents. In some embodiments, a pharmaceutical composition is a liquid solution, suspension, emulsion, tablet, pill, capsule, sustained release formulation, or powder. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

In some embodiments, an immunogenic composition is formulated for intradermal injection, intranasal administration or intramuscular injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules, and. General considerations in the formulation and manufacture of pharmaceutical agents for administration by these routes may be found, for example, in *Remington's Pharmaceutical Sciences*, 19$^{th}$ ed., Mack Publishing Co., Easton, Pa., 1995; incorporated herein by reference. At present the oral or nasal spray or aerosol route (e.g., by inhalation) is most commonly used to deliver therapeutic agents directly to the lungs and respiratory system. In some embodiments, compositions in accordance with the invention are administered using a device that delivers a metered dosage of composition (e.g., of an optimized HA polypeptide). Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference). Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical mantoux method of intradermal administration.

Preparations for parenteral administration include sterile aqueous or nonaqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Co-Administration of Optimized H5N1 Influenza HA Polypeptides to Elicit an Immune Response Further provided are the use and methods of co-administration (e.g., immunogenic cocktail compositions or prime-boost regimens) described herein in the prophylactic or therapeutic treatment of H5N1 influenza infection; e.g., methods of generating or eliciting an immune response to influenza virus in a subject by co-administering optimized H5N1 influenza HA polypeptides, VLPs containing the optimized H5N1 influenza HA polypeptides, fusion protein or inactivated influenza virus (e.g., split-inactivated), or live attenuated influenza virus (e.g., temperature sensitive virus) as disclosed herein (e.g., cocktails of the HA polypeptides that appear in Table 1). In certain embodiments, the optimized H5N1 influenza HA polypeptides are co-administered to the subject as a combination or cocktail (i.e., at the same time). In other embodiments, the optimized H5N1 influenza HA polypeptides are co-administered sequentially either as individual polypeptides or as cocktails. For example, certain methods of eliciting an immune response in a subject comprise administering to the subject a priming vaccine comprising a first optimized H5N1 influenza HA polypeptide as described herein followed by administering a boosting vaccine comprising a second optimized H5N1 influenza HA polypeptide as described herein, where the second optimized H5N1 influenza HA polypeptide is different than the first optimized H5N1 influenza HA polypeptide. In some embodiments, the first priming vaccine comprises a live, attenuated virus (e.g., temperature sensitive virus) containing the first optimized H5N1 influenza HA polypeptide and the second boosting vaccine comprises the second optimized H5N1 influenza HA polypeptide, for example, a VLP containing the second optimized H5N1 influenza HA polypeptide.

In some embodiments, the HA protein, HA fusion protein, VLP or virus can be administered using any suitable route of administration, such as, for example, intramuscular, intranasal or oral. In some embodiments, the HA protein, fusion protein, VLP or virus is administered as a composition further comprising a pharmaceutically acceptable carrier and/or an adjuvant.

The uses and methods of the compositions described herein can include selecting a subject (e.g., a human subject) in need of treatment. Compositions comprising the optimized influenza HA polypeptides may be administered prior to or after development of one or more symptoms of an H5N1 influenza infection. Administration can be systemic or local. That is, in some embodiments, the compositions described herein may be administered prophylactically to prevent H5N1 influenza infection or ameliorate the symptoms of a potential H5N1 influenza infection. In some embodiments, a subject is at risk of H5N1 influenza virus infection if the subject will be in contact with other individuals or livestock (e.g., birds) known or suspected to have been infected with pandemic influenza virus and/or if the subject will be present in a location in which H5N1 influenza infection is known or thought to be prevalent or endemic. In some embodiments, the compositions are administered to a subject considered to be suffering from an H5N1 influenza infection, or the subject is displaying one or more symptoms commonly associated with influenza infection. In some embodiments, the subject is known or believed to have been exposed to the H5N1 influenza virus. In some embodiments, a subject is considered to be at risk or susceptible to an H5N1 influenza infection if the subject is known or believed to have been exposed to the influenza virus. In some embodiments, a subject is known or believed to have been exposed to the H5N1 influenza virus if the subject has been in contact with other individuals or livestock (e.g., birds) known or suspected to have been infected with pandemic influenza virus and/or if the subject is or has been present in a location in which H5N1 influenza infection is known or thought to be prevalent or endemic.

Immunogenic compositions in accordance with the invention may be administered in any dose appropriate to achieve a desired outcome. In some embodiments, the desired outcome is induction of a lasting adaptive immune response against multiple H5N1 influenza strains. In some embodiments, the desired outcome is reduction in intensity, severity, and/or frequency, and/or delay of onset of one or more symptoms of H5N1 influenza infection. The dose required may vary from subject to subject depending on the species, age, weight and general condition of the subject, the severity of the infection being treated, the particular composition being used and its mode of administration.

In some embodiments of the methods of eliciting an immune response or immunizing a subject, the subject is administered a composition comprising about 15 to about 45 μg of hemagglutinin antigen component from each of the H5N1 COBRAs (i.e., 15-45 μg each of Human COBRA-2, All H5 COBRA and Human/Avian COBRA-2 in a cocktail). In particular examples, the subject is administered a composition comprising about 15 μg, about 20 μg, about 25 μg, about 30 μg, about 35 μg, about 40 μg, or about 45 μg of each of the optimized H5N1 influenza HA polypeptides in a given cocktail. For example, if a vaccine comprises a H5N1 influenza HA antigen cocktail consisting of two of the HA polypeptides in Table 1, a subject may receive a total amount of 30-90 μg (15-45 μg for each of the two) of influenza HA. In one specific non-limiting example, the subject is administered about 15 μg of each of the optimized H5N1 influenza HA polypeptides. In particular examples, the subject is administered a composition comprising a total hemagglutinin antigen component of about 45 to about 90 μg. Dosages may be measured by, for example, single radial immunodiffusion (SRD) (J. M. Wood, et al.: *An improved single radial immunodiffusion technique for the assay of influenza haemagglutinin antigen: adaptation for potency determination of inactivated whole virus and subunit vaccines, J. Biol. Stand.,* 1977, 5:237-247; J. M. Wood, et al., *International collaborative study of single radial diffusion and immuno-electrophoresis techniques for the assay of haemagglutinin antigen of influenza virus, J. Biol. Stand.,* 1981, 9:317-330).

In some embodiments, the present invention provides for the immunogenic compositions (e.g., vaccines) described herein to be administered to a human subject. In particular embodiments, a human subject is 6 months of age or older, is 6 months through 35 months of age, is 36 months through 8 years of age, or 9 years of age or older.

In some embodiments, immunogenic compositions in accordance with the invention are administered in single or multiple doses. In some embodiments, pharmaceutical compositions in accordance with the invention are administered in multiple doses administered on different days (e.g., prime-boost vaccination strategies). In some embodiments, pharmaceutical compositions in accordance with the invention are administered according to a continuous dosing regimen, such that the subject does not undergo periods of less than therapeutic dosing interposed between periods of therapeutic dosing. In some embodiments, pharmaceutical compositions in accordance with the invention are administered according to an intermittent dosing regimen, such that the subject undergoes at least one period of less than therapeutic dosing interposed between two periods of therapeutic dosing.

The methods and uses of the immunogenic compositions described herein include prime-boost vaccination strategies. Prime-boost vaccination comprises administering a priming vaccine and then, after a period of time has passed, administering to the subject a boosting vaccine. The immune response is "primed" upon administration of the priming vaccine, and is "boosted" upon administration of the boosting vaccine. The priming vaccine can include any of the immunogenic HA polypeptides, and/or compositions or cocktails thereof described herein. Likewise, the boosting vaccine can include any of the immunogenic cocktails described herein.

For example, the priming vaccine may comprise a combination of at least two recombinant H5N1 influenza hemagglutinin (HA) polypeptides selected from the group consisting of: a recombinant, optimized influenza HA polypeptide comprising an amino acid sequence at least 99.8% identical to SEQ ID NO: 1, a recombinant, optimized influenza HA polypeptide comprising an amino sequence at least 99.6% identical to SEQ ID NO: 3, and a recombinant, optimized influenza HA polypeptide comprising an amino sequence at least 99% identical to SEQ ID NO: 5; the boosting vaccine may comprise the same immunogenic composition. In some embodiments, the priming vaccine comprises a combination of at least two recombinant H5N1 influenza hemagglutinin (HA) polypeptides selected from the group consisting of: a recombinant, optimized influenza HA polypeptide comprising an amino acid sequence at least 99.8% identical to residues 2-566 of SEQ ID NO: 1, a recombinant, optimized influenza HA polypeptide comprising an amino acid sequence at least 99.6% identical to residues 2-567 of SEQ ID NO: 3, and a recombinant, optimized influenza HA polypeptide comprising an amino sequence is least 99% identical to amino acids 2-568 of SEQ ID NO: 5; the boosting vaccine may comprise the same immunogenic composition. In some embodiments, the priming vaccine comprises a combination of at least two recombinant H5N1 influenza hemagglutinin (HA) polypeptides selected from the group consisting of: a recombinant, optimized influenza HA polypeptide comprising an amino acid sequence at least 99.8% identical to residues 2-566 of SEQ ID NO: 1, a recombinant, optimized influenza HA polypeptide comprising an amino acid sequence at least 99.6% identical to residues 2-567 of SEQ ID NO: 3, and a recombinant, optimized influenza HA polypeptide comprising an amino sequence is least 99% identical to amino acids 2-568 of SEQ ID NO: 5; the boosting vaccine may be a composition comprising a combination of recombinant H5N1 influenza HA polypeptides consisting only of a recombinant, optimized influenza HA polypeptide comprising an amino acid sequence at least 99.8% identical to residues 2-566 of SEQ ID NO: 1 and a recombinant, optimized influenza HA polypeptide comprising an amino acid sequence at least 99.6% identical to residues 2-567 of SEQ ID NO: 3. In some embodiments, the boosting vaccine comprises or consists of the same optimized H5N1 influenza polypeptide(s) as the priming vaccine. For example, in some embodiments, both the priming vaccine and the boosting vaccine comprise computationally optimized H5N1 HA polypeptides selected from the group consisting of: HA polypeptides that are at least 95%, at least 96%, at least 97%, at least 98%, or at least 99% identical to SEQ ID NO: 1 and SEQ ID NO: 3 and SEQ ID NO: 5; and/or at least 95%, at least 96%, at least 97%, at least 98%, or at least 99% identical to residues 2-566 of SEQ ID NO: 1 and residues 2-567 of SEQ ID NO: 3 and residues 2-568 of SEQ ID NO: 5. In some embodiments, the boosting vaccine and the priming vaccine may contain different cocktails of optimized H5N1 influenza HA polypeptides as described herein. These prime-boost cocktail combinations are summarized in the table below, where:

All H5N1 COBRA="1"
Human/Avian COBRA-2="3"
Human COBRA-2="5"

| Same Cocktails in Prime/Boost | |
|---|---|
| Prime | Boost |
| 1/3 | 1/3 |
| 1/5 | 1/5 |
| 3/5 | 3/5 |
| 1/3/5 | 1/3/5 |

| Different Cocktails in Prime/Boost | |
|---|---|
| Prime | Boost |
| 1/3 | 3/5 |
| 3/5 | 1/3 |
| 1/5 | 1/3 |
| 1/3 | 1/5 |
| 1/5 | 3/5 |
| 3/5 | 1/5 |
| 1/3/5 | 1/3 |
| 1/3/5 | 1/5 |
| 1/3/5 | 3/5 |
| 1/3 | 1/3/5 |
| 1/5 | 1/3/5 |
| 3/5 | 1/3/5 |

In some embodiments, the priming vaccine cocktail comprises an adjuvant. In some embodiments, the boosting vaccine cocktail comprises an adjuvant.

The priming vaccine and boosting vaccine can each include a different optimized H5N1 influenza HA polypeptide as described herein. For example, the priming vaccine may comprise an optimized H5N1 influenza hemagglutinin (HA) polypeptide comprising an amino acid sequence at least 99.8% identical to SEQ ID NO: 1 or residues 2-566 of SEQ ID NO: 1 and the boosting vaccine may comprise a H5N1 influenza hemagglutinin (HA) polypeptide selected from the group consisting of: a recombinant, optimized influenza HA polypeptide comprising an amino sequence at least 99.6% identical to SEQ ID NO: 3 or residues 2-567 of SEQ ID NO: 3, and a recombinant, optimized influenza HA polypeptide comprising an amino sequence at least 99% identical to SEQ ID NO: 5 or residues 2-568 of SEQ ID NO:

5. In certain embodiments, the priming vaccine comprises or consists of a first recombinant, optimized H5N1 influenza HA polypeptide comprising the amino acid sequence of SEQ ID NO: 1 or residues 2-566 of SEQ ID NO: 1 and the boosting vaccine comprises or consists of a second recombinant, optimized H5N1 influenza HA polypeptide comprising an amino acid sequence selected from the group consisting of: the amino acid sequence of SEQ ID NO: 3, residues 2-567 of SEQ ID NO: 3, SEQ ID NO: 5, and residues 2-568 of SEQ ID NO: 5.

In other embodiments, the priming vaccine may comprise an optimized H5N1 influenza hemagglutinin (HA) polypeptide comprising an amino acid sequence at least 99.6% identical to SEQ ID NO: 3 or at least 99.6% identical to residues 2-567 of SEQ ID NO: 3 and the boosting vaccine may comprise a H5N1 influenza hemagglutinin (HA) polypeptide selected from the group consisting of: a recombinant, optimized influenza HA polypeptide comprising an amino sequence at least 99.8% identical to SEQ ID NO: 1 or residues 2-566 of SEQ ID NO: 1, and a recombinant, optimized influenza HA polypeptide comprising an amino sequence at least 99% identical to SEQ ID NO: 5 or residues 2-568 of SEQ ID NO: 5. In certain embodiments, the priming vaccine comprises or consists of a first recombinant, optimized H5N1 influenza HA polypeptide comprising the amino acid sequence of SEQ ID NO: 3 or residues 2-567 of SEQ ID NO: 3 and the boosting vaccine comprises or consists of a second recombinant, optimized H5N1 influenza HA polypeptide comprising an amino acid sequence selected from the group consisting of: the amino acid sequence of SEQ ID NO: 1, residues 2-566 of SEQ ID NO: 1, SEQ ID NO: 5, and residues 2-568 of SEQ ID NO: 5.

In other embodiments, the priming vaccine may comprise an optimized H5N1 influenza hemagglutinin (HA) polypeptide comprising an amino acid sequence at least 99% identical to SEQ ID NO: 5 or residues 2-568 of SEQ ID NO: 5 and the boosting vaccine may comprise a H5N1 influenza hemagglutinin (HA) polypeptide selected from the group consisting of: a recombinant, optimized influenza HA polypeptide comprising an amino sequence at least 99.8% identical to SEQ ID NO: 1 or residues 2-566 of SEQ ID NO: 1, and a recombinant, optimized influenza HA polypeptide comprising an amino sequence at least 99.6% identical to SEQ ID NO: 3 or at least 99.6% identical to residues 2-567 of SEQ ID NO: 3. In certain embodiments, the priming vaccine comprises or consists of a first recombinant, optimized H5N1 influenza HA polypeptide comprising the amino acid sequence of SEQ ID NO: 5 or residues 2-567 of SEQ ID NO: 3 and the boosting vaccine comprises or consists of a second recombinant, optimized H5N1 influenza HA polypeptide comprising an amino acid sequence selected from the group consisting of: the amino acid sequence of SEQ ID NO: 1, residues 2-566 of SEQ ID NO: 1, SEQ ID NO: 3, and residues 2-567 of SEQ ID NO: 3.

In some embodiments, the methods of eliciting an immune response in or immunizing a subject comprise:

administering a priming vaccine comprising a first recombinant, optimized t H5N1 influenza HA polypeptide comprising an amino acid sequence at least 99.8% identical to SEQ ID NO: 1; and administering a boosting vaccine comprising a second recombinant, optimized H5N1 influenza HA polypeptide comprising an amino acid sequence at least 99.6% identical to SEQ ID NO: 3. In certain embodiments, the first recombinant, optimized H5N1 influenza HA polypeptide comprises an amino acid sequence at least 99.8% identical to residues 2-566 of SEQ ID NO: 1 and the second recombinant, optimized H5N1 influenza HA polypeptide comprises an amino acid sequence at least 99.6% identical to residues 2-567 of SEQ ID NO: 3. In other embodiments, the first recombinant, optimized H5N1 influenza HA polypeptide comprises the amino acid sequence of SEQ ID NO: 1 or residues 2-566 of SEQ ID NO: 1 and the second recombinant, optimized H5N1 influenza HA polypeptide comprises the amino acid sequence of SEQ ID NO: 3 or residues 2-567 of SEQ ID NO: 3.

In some embodiments the methods of eliciting an immune response in or immunizing a subject comprise:

administering a priming vaccine comprising a first recombinant, optimized H5N1 influenza HA polypeptide comprising an amino acid sequence at least 99.8% identical to SEQ ID NO: 1; and administering a boosting vaccine comprising a second recombinant, optimized H5N1 influenza HA polypeptide comprising an amino acid sequence at least 99% identical to SEQ ID NO: 5. In certain embodiments, the first recombinant, optimized H5N1 influenza HA polypeptide comprises an amino acid sequence at least 99.8% identical to residues 2-566 of SEQ ID NO: 1 and the second recombinant, optimized H5N1 influenza HA polypeptide comprises an amino acid sequence at least 99% identical to residues 2-568 of SEQ ID NO: 5. In other embodiments, the first recombinant, optimized H5N1 influenza HA polypeptide comprises the amino acid sequence of SEQ ID NO: 1 or residues 2-566 of SEQ ID NO: 1 and the second recombinant, optimized H5N1 influenza HA polypeptide comprises the amino acid sequence of SEQ ID NO: 5 or residues 2-568 of SEQ ID NO: 5.

In some embodiments the methods of eliciting an immune response in or immunizing a subject comprise:

administering a priming vaccine comprising a first recombinant, optimized H5N1 influenza HA polypeptide comprising an amino acid sequence at least 99.6% identical to SEQ ID NO: 3; and administering a boosting vaccine comprising a second recombinant, optimized H5N1 influenza HA polypeptide comprising an amino acid sequence at least 99% identical to SEQ ID NO: 5. In certain embodiments, the first recombinant, optimized H5N1 influenza HA polypeptide comprises an amino acid sequence at least 99.6% identical to residues 2-567 of SEQ ID NO: 3 and the second recombinant, optimized H5N1 influenza HA polypeptide comprises an amino acid sequence at least 99% identical to residues 2-568 of SEQ ID NO: 5. In other embodiments, the first recombinant, optimized H5N1 influenza HA polypeptide comprises the amino acid sequence of SEQ ID NO: 3 or residues 2-567 of SEQ ID NO: 3 and the second recombinant, optimized H5N1 influenza HA polypeptide comprises the amino acid sequence of SEQ ID NO: 5 or residues 2-568 of SEQ ID NO: 5.

In some embodiments the methods of eliciting an immune response in or immunizing a subject comprise:

administering a priming vaccine comprising a first recombinant, optimized H5N1 influenza HA polypeptide comprising an amino acid sequence at least 99.6% identical to SEQ ID NO: 3; and administering a boosting vaccine comprising a second recombinant, optimized H5N1 influenza HA polypeptide comprising an amino acid sequence at least 99.8% identical to SEQ ID NO: 1. In certain embodiments, the first recombinant, optimized H5N1 influenza HA polypeptide comprises an amino acid sequence at least 99.6% identical to residues 2-567 of SEQ ID NO: 3 and the second recombinant, optimized H5N1 influenza HA polypeptide comprises an amino acid sequence at least 99.8% identical to residues 2-566 of SEQ ID NO: 1. In other embodiments, the first recombinant, optimized H5N1 influenza HA polypeptide comprises the amino acid sequence of SEQ ID NO: 3 or residues 2-567 of SEQ ID NO: 3 and the second recombinant, optimized H5N1 influenza HA polypeptide comprises the amino acid sequence of SEQ ID NO: 1 or residues 2-566 of SEQ ID NO: 1.

In some embodiments the methods of eliciting an immune response in or immunizing a subject comprise:

administering a priming vaccine comprising a first recombinant, optimized H5N1 influenza HA polypeptide comprising an amino acid sequence at least 99% identical to SEQ ID NO: 5; and administering a boosting vaccine comprising a second recombinant, optimized H5N1 influenza HA polypeptide comprising an amino acid sequence at least 99.8% identical to SEQ ID NO: 1. In certain embodiments, the first recombinant, optimized H5N1 influenza HA polypeptide comprises an amino acid sequence at least 99% identical to residues 2-568 of SEQ ID NO: 5 and the second recombinant, optimized H5N1 influenza HA polypeptide comprises an amino acid sequence at least 99.8% identical to residues 2-566 of SEQ ID NO: 1. In other embodiments, the first recombinant, optimized H5N1 influenza HA polypeptide comprises the amino acid sequence of SEQ ID NO: 5 or residues 2-568 of SEQ ID NO: 5 and the second recombinant, optimized H5N1 influenza HA polypeptide comprises the amino acid sequence of SEQ ID NO: 1 or residues 2-566 of SEQ ID NO: 1.

In some embodiments the methods of eliciting an immune response in or immunizing a subject comprise:

administering a priming vaccine comprising a first recombinant, optimized H5N1 influenza HA polypeptide comprising an amino acid sequence at least 99% identical to SEQ ID NO: 5; and administering a boosting vaccine comprising a second recombinant, optimized H5N1 influenza HA polypeptide comprising an amino acid sequence at least 99.6% identical to SEQ ID NO: 3. In certain embodiments, the first recombinant, optimized H5N1 influenza HA polypeptide comprises an amino acid sequence at least 99% identical to residues 2-568 of SEQ ID NO: 5 and the second recombinant, optimized H5N1 influenza HA polypeptide comprises an amino acid sequence at least 99.6% identical to residues 2-567 of SEQ ID NO: 3. In other embodiments, the first recombinant, optimized H5N1 influenza HA polypeptide comprises the amino acid sequence of SEQ ID NO: 5 or residues 2-568 of SEQ ID NO: 5 and the second recombinant, optimized H5N1 influenza HA polypeptide comprises the amino acid sequence of SEQ ID NO: 3 or residues 2-567 of SEQ ID NO: 3.

The booster vaccine is administered to the subject after the primer vaccine. Administration of the priming vaccine and the boosting vaccine can be separated by any suitable timeframe. For example, the booster vaccine can be administered 1 week, 2 weeks, 3 weeks, 4 weeks, 5 weeks, or 6 weeks, or a range defined by any two of the foregoing values, following administration of the priming vaccine. The dose of the priming vaccine and boosting vaccine administered to a subject depends on a number of factors, including the extent of any side-effects, the particular route of administration, and the like. In certain embodiments, the dose of the priming vaccine comprises about 15-45 µg (e.g., about 15, 20, 25, 30, 35, 40, or 45 µg) of the recombinant, optimized H5N1 influenza HA polypeptide. In certain embodiments, the dose of the boosting vaccine comprises about 15-45 µg (e.g., about 15, 20, 25, 30, 35, 40, or 45 µg) of the recombinant, optimized H5N1 influenza HA polypeptide. In some embodiments, the dose of the boosting vaccine is the same as the dose of the priming vaccine.

Immunogenic compositions of the present invention may be administered either alone or in combination with one or more other therapeutic agents including, but not limited to, other vaccines and/or antibodies. By "in combination with," it is not intended to imply that the agents must be administered at the same time or formulated for delivery together, although these methods of delivery are within the purview of the present invention. In general, each agent will be administered at a dose and on a time schedule determined for that agent. In some embodiments, pharmaceutical compositions in accordance with the invention and/or optimized HA polypeptides as described herein are administered in combination with one or more of an anti-viral agent (e.g., Oseltamivir [TAMIFLU®], Zanamavir [RELEZA®], etc.) and/or a sialidase.

In some embodiments, co-administration (e.g., the immunogenic cocktail compositions or prime-boost regimens) elicit a protective immune response against at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 different H5N1 influenza strains. In particular embodiments, "eliciting a protective immune response" can be ascertained, for example, by using the generally known hemagglutination inhibition assay (HAI) as a surrogate measure of influenza vaccine efficacy. HAI assays may use chicken, turkey or horse erythrocytes for the detection of antibodies specific for H5N1. In particular embodiments, protective immune responses are demonstrated by eliciting an average HAI titer of greater than 1:40, which has been correlated with prevention and reduction of influenza illness. In some embodiments, the immunogenic compositions described herein elicit an HAI antibody titer of at least 1:30, 1:40, 1:50, 1:60, or within a range of 1:30-1:60 or 1:40-1:60, when administered to a subject for prophylaxis or treatment of influenza infection. HAI antibody titers of approximately 1:32 to 1:40 will generally protect about 50% of subjects from infection after immunization with inactivated human influenza virus vaccine. When converting log 2 data, a value slightly less than 5.5 corresponds to an HAI antibody titer of 1:40. However, serum HAI antibody titers as low as 1:8 have been shown to provide resistance to infection with human influenza viruses, which indicates that the levels of antibody required for protection may be fairly low (Treanor, J. & Wright, P. F. *Immune correlates of protection against influenza in the human challenge model. Dev. Biol. (Basel)*, 2003, 115:97-104; incorporated by reference herein).

In some embodiments, elicitation of a protective immune response can by identified by seroconversion rates. In particular embodiments, a protective level of seroconversion is defined as at least a 4-fold rise in HAI titer, for example, a pre-administration or vaccination HAI titer of less than 1:10 and a post vaccinate titer of greater than or equal to 1:40. In other words, successful rates of seroconversion may be defined as the percentage of subjects with either a pre-vaccination HAI titer less than about 1:10 and a post-vaccination HAI titer of greater than about 1:40 or a pre-vaccination HAI titer greater than about 1:10 and a minimum four-fold rise in post-vaccination HAI antibody titer. In particular embodiments, the immunogenic compositions described herein elicit a seroconversion rate of at least a 3-fold 4-fold, at least a 5-fold, at least a 6-fold, etc.

rise in HAI titer when administered to a subject for prophylaxis or treatment of influenza infection. In particular embodiments, the immunogenic compositions improve seroconversion (measured by HAI) by at least 30%, at least 40%, at least 50%, at least 60%, at least 70%, at least 80% or at least 90% when administered to a subject for prophylaxis or treatment of influenza infection. In some embodiments, co-administration (e.g., immunogenic cocktail compositions or prime-boost regimens) generates a protective immune response that spans at least 5, at least 6, at least 7, at least 8, at least 9, at least 10 or at least 11 (e.g., 11) different clades and subclades of H5N1 influenza.

Animal Testing

The present invention provides methods for testing optimized HA polypeptides in accordance with the invention in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, guinea pigs, rabbits, and rats. In some embodiments, an animal host used for the invention is a ferret. In particular, in some embodiments, an animal host is naïve to viral exposure or infection prior to administration of a binding agent in accordance with the invention (optionally in a composition in accordance with the invention). In some embodiments, the animal host is inoculated with, infected with, or otherwise exposed to influenza virus prior to or concurrent with co-administration (e.g., immunogenic cocktail composition or prime-boost regimen) of optimized H5N1 HA polypeptides described herein. An animal host used in the practice of the present invention can be inoculated with, infected with, or otherwise exposed to influenza virus by any method known in the art. In some embodiments, an animal host may be inoculated with, infected with, or exposed to virus intranasally. In some embodiments, an animal host may be a bird, such as a chicken.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey et al., 2007, *Science* 315; 655-59; incorporated herein by reference). Virus transmission studies may be used to test computationally optimized HA polypeptides in accordance with the invention. For example, cocktails of computationally optimized HA polypeptides described herein or prime-boost regimens of different, individual COBRAs may be administered to a suitable animal host in order to determine the efficacy of said cocktails or prime-boost regimens in eliciting a broad immune response in the animal host. Using information gathered from studies in an animal host, one may predict the efficacy of said cocktails or prime-boost regimens to elicit broadly protective in a human host.

The present invention will be more fully understood by reference to the following Examples. All literature citations are incorporated by reference.

EXAMPLES

Example 1—Antigen Construction and Synthesis

Influenza A HA nucleotide sequences isolated from human H5N1 infections were downloaded from the NCBI Influenza Virus Resource database (see supporting materials for complete list of accession numbers and isolate descriptions). Nucleotide sequences were translated into protein sequences using the standard genetic code. Full-length sequences from H5N1 clade 2 human infections from 2004 to 2006 were acquired and used for subsequent consensus generations. For each round of consensus generation, multiple alignment analysis was applied and the consensus sequence was generated using AlignX (Vector NTI). The final amino acid sequence, termed computationally optimized broadly reactive antigen (COBRA), was reverse translated and optimized for expression in mammalian cells, including codon usage and RNA optimization (GeneArt; Regensburg, Germany). This construct was then synthesized and inserted into the pTR600 expression vector.

Figures 2A, 2B:
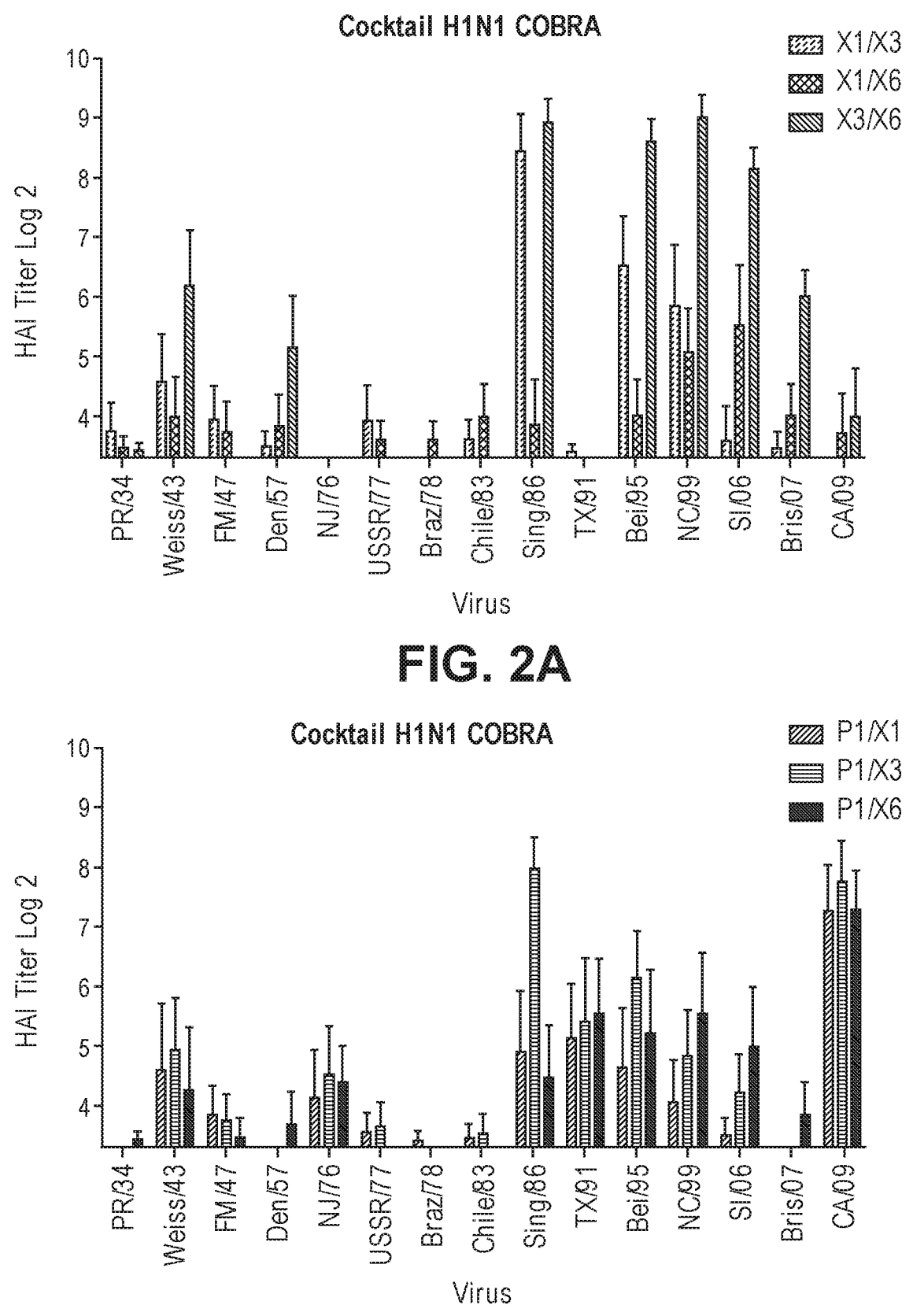
Figures 2C, 2D:
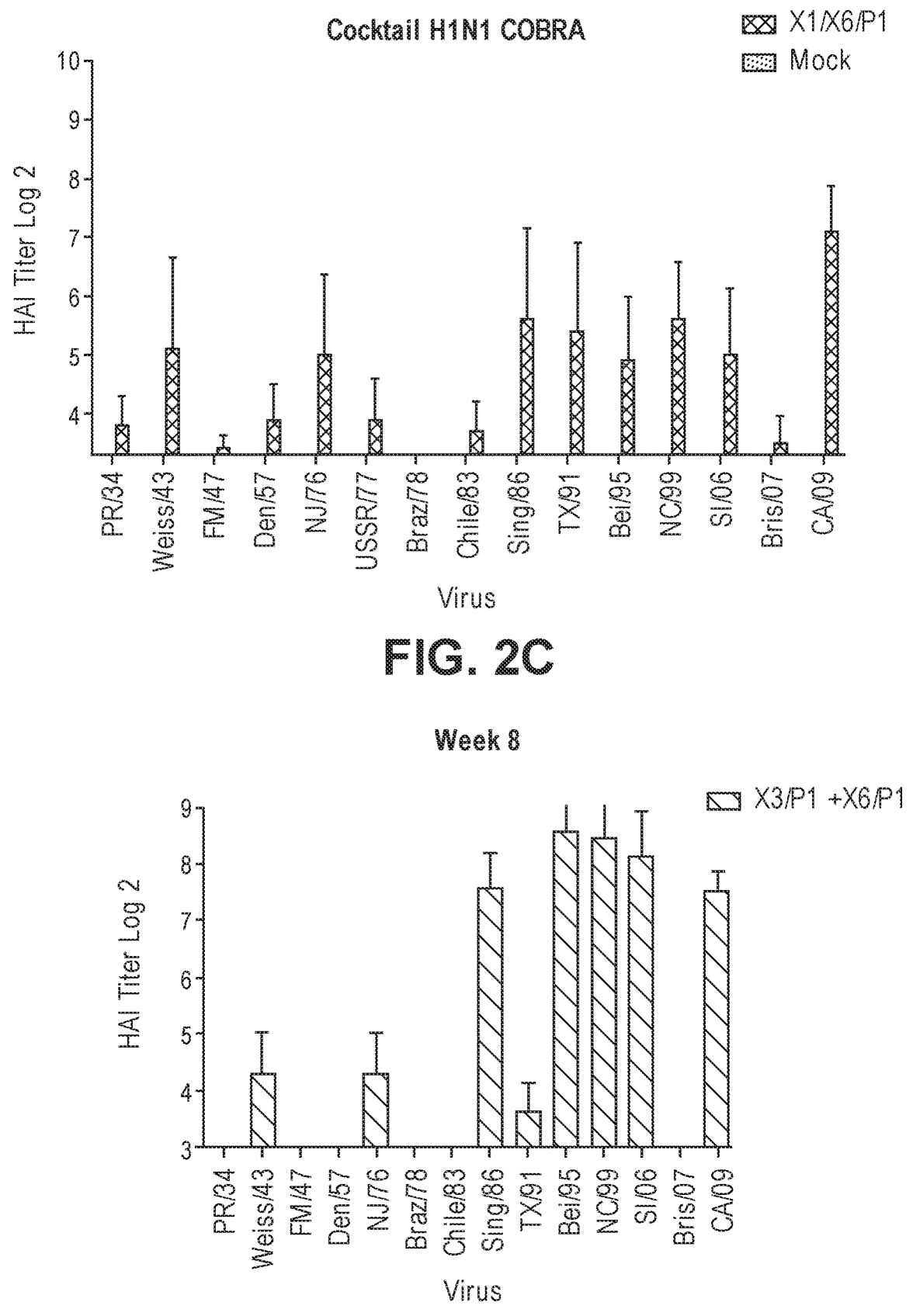

The design and characterization of the computationally optimized broadly reactive antigen (COBRA) has been described previously (see, e.g., Giles, B. M. and T. M. Ross, *Development of a computationally optimized broadly reactive (COBRA) hemagglutinin for elicitation of protective antibodies against multiple clades of H5N1*. Vaccine, 2011. 29: p. 3043-3054). Briefly, this second generation of COBRA HA antigen was generated by multiple rounds of consensus generation using avian and human HA sequences from multiple H5N1 clades leading to infections between 2004 and 2010. COBRA HA antigens were designed to represent 1) human clade 2 isolates, 2) human and avian clade 2 isolates, and 3) all clades of H5N1. Unique hemagglutinin (HA) sequences (525) were downloaded from the NCBI Influenza Virus Resource (IVR) sequence database. The sequences were first grouped into phylogenetic subclades. HA amino acid sequences for each individual outbreak group were aligned and the most common amino acid at each position was determined resulting in primary consensus sequences representing each outbreak group within each subclade (FIG. 1). Each COBRA HA structure was generated using the 3D-JIGSAW algorithm and renderings were performed using MacPyMol (FIG. 2A). A phylogenetic tree was inferred from hemagglutinin amino acid sequences using the maximum likelihood method and clade/sub-clade groupings were identified using Jalview (Dundee, UK) (FIG. 2B).

Example 2—In Vitro Expression

Human embryonic kidney (HEK) 293T cells ($1\times10^6$) were transiently transfected with 3 μg DNA expressing COBRA HA. Cells were incubated for 72 h at 37° C. and then lysed with 1% Triton-X 100 and clarified supernatant harvested following centrifugation. Cell lysates were then electrophoresed on a 10% SDS-PAGE gel and transferred to a PVDF membrane. The blot was probed with pooled mouse antisera from infections with 6:2 reassortant H5N1 viruses expressing HA derived from either A/Vietnam/1203/2004 or A/Whooper Swan/244/2005. HA-antibody complexes were then detected using goat anti-mouse IgG HRP (Southern Biotech; Birmingham, Ala., USA). HRP activity was detected using chemiluminescent substrate (Pierce Biotechnology; Rockford Ill., USA) and exposed to X-ray film (ThermoFisher; Pittsburgh, Pa., USA).

Example 3—Functional Characterization

To determine receptor-binding characteristics, virus-like particles (VLPs) containing COBRA HA proteins were purified from the supernatants of mammalian cell lines as previously described. HEK 293T cells were transiently transfected with plasmids expressing HIV Gag, COBRA HA and neuraminidase (NA, A/Thailand/1(KAN-1)/2004) and incubated for 72 h at 37° C. Supernatants were collected and VLPs were purified via ultracentrifugation (100,000×g through 20% glycerol, weight per volume) for 4 h at 4° C. The pellets were subsequently resuspended in phosphate buffered saline PBS, pH 7.2 and stored at −80° C. until use. Protein concentration was determined by Micro BCA™ Protein Assay Reagent Kit (Pierce Biotechnology, Rockford, Ill., USA). COBRA HA VLPs were prepared in various amounts as measured by total HA protein and each individual preparation was two-fold serially diluted in v-bottom microtiter plates. An equal volume of 1% horse erythrocytes (RBC) (Lampire; Pipersville, Pa., USA) in PBS was added to the diluted VLPs and incubated for 60 minutes at room temperature. The HA titer was determined by the reciprocal dilution of the last well which contained agglutinated RBC.

To determine endosomal fusion characteristics, COBRA-pseudotyped lentiviral vectors expressing a luciferase reporter gene were produced as described. Briefly, 293T cells were co-transfected by using the following plasmids: 7 μg of pCMVdeltaR8.2, 7 μg of pHR-CMV-Luc, 3 μg pCMV/R N1 (Kan-1) (all kindly provided by Dr. G. Nabel) and 3 ug pTR600 COBRA HA. Cells were transiently transfected and incubated for 72 h at 37° C. Supernatants were harvested, centrifuged to clear cell debris, filtered through a 0.22 μm syringe filter, aliquotted, and used immediately or frozen at −80° C. For fusion assays, 100 μl of pseudoviruses were added to confluent MDCK cells in 48-well plates (~30,000 cells per well). Plates were incubated at room temperature for 30 min, washed, and fresh medium added. Forty-eight hours after infection, cells were lysed in mammalian cell lysis buffer (Promega; Madison, Wis., USA). A standard quantity of cell lysate was used in a luciferase assay with luciferase assay reagent (Promega; Madison, Wis., USA) according to the manufacturer's protocol.

Example 4—Vaccine Preparation

HEK 293T cells were transiently transfected with plasmids expressing M1 (A/Puerto Rico/8/1934, optimized for expression in mammalian cells), NA (A/Thailand/1(KAN-1)/2004, optimized for expression in mammalian cells) and COBRA H5 HA and incubated for 72 h at 37° C. Supernatants were collected and cell debris removed by low speed centrifugation followed by vacuum filtration through a 0.22 μm sterile filter. VLPs were purified via ultracentrifugation (100,000×g through 20% glycerol, weight per volume) for 4 h at 4° C. The pellets were subsequently resuspended in PBS pH 7.2 and stored in single use aliquots at −80° C. until use. Total protein concentration was determined by Micro BCA™ Protein Assay Reagent Kit (Pierce Biotechnology, Rockford, Ill., USA).

HA specific content was determined by western blot and densitometry. Purified recombinant COBRA HA and purified VLPs were prepared in standard total protein amounts and were electrophoresed on a 10% SDS-PAGE gel and transferred to a PVDF membrane. The blot was probed with mouse polyclonal antisera pooled from mice infected with 6:2 reassortant H5N1 viruses with the surface glycoproteins derived from either A/Vietnam/1203/2004 or A/Whooper Swan/244/2005 and the HA-antibody complexes were detected using a goat anti-mouse IgG conjugated to horse radish peroxidase (HRP) (Southern Biotech; Birmingham, Ala., USA). HRP was detected by chemiluminescent substrate (Pierce Biotechnology; Rockford Ill., USA) and exposed to X-ray film (ThermoFisher; Pittsburgh, Pa., USA). Density of bands was determined using ImageJ software (NIH). Density of recombinant HA bands were used to calculate a standard curve and the density of the purified VLPs was interpolated using the results from the recombinant HA. Experiments were performed in triplicate and multiple exposure times were analyzed for all iterations.

Example 5—Mouse Studies

BALB/c mice (*Mus musculis*, females, 6-8 weeks) were purchased from Harlan Sprague Dawley, (Indianapolis, Ind., USA) and housed in microisolator units and allowed free access to food and water and were cared for under USDA guidelines for laboratory animals. For dosing studies, mice (12 mice per group) were vaccinated with one of two doses of purified VLPs (3.0 μg or 0.6 μg), based upon HA content from the densitometry assay, via intramuscular injection at week 0 and then boosted with the same dose at week 4. For comparison studies, mice (12 mice per group) were vaccinated with purified VLPs (3 μg), based upon HA content from the densitometry assay, via intramuscular injection at week 0 and then boosted with the same dose at week 4. Vaccines at each dose were formulated with Imject® alum adjuvant (Imject® Alum, Pierce Biotechnology; Rockford, Ill., USA) according to the manufacturer's protocol or vehicle alone. Fourteen to twenty-one days after each vaccination, blood was collected from anesthetized mice via the retro-orbital plexus and transferred to a microfuge tube. Tubes were centrifuged and sera was removed and frozen at −20±5° C.

Three weeks after final vaccination, mice were challenged intranasally with $5 \times 10^3$ plaque forming units (PFU) of the highly pathogenic H5N1 virus A/Whooper Swan/Mongolia/244/2005 (Clade 2.2) in a volume of 50 μl. The challenge dose represents approximately 50 $LD_{50}$ in mice. After infection, mice were monitored daily for weight loss, disease signs and death for 14 days after infection. At days 2 and 3 post-infection, 5 mice were sacrificed per time point for determination of viral lung titers. Individual body weights, sickness scores and death were recorded for each group on each day after inoculation. Sickness score was determined by evaluating activity (0=normal, 1=reduced, 2=severely reduced), hunched back (0=absent, 1=present) and ruffled fur (0=absent, 1=present). Experimental endpoint was defined as greater than 20% weight loss or display of neurological disease such as hind limb paralysis. All H5N1 influenza virus studies were performed under high-containment biosafety level 3 enhanced conditions (BSL3+). All procedures were in accordance with the NRC Guide for the Care and Use of Laboratory Animals, the Animal Welfare Act, and the CDC/NIH Biosafety in Microbiological and Biomedical Laboratories.

Example 6—ELISA Assay

The ELISA assay was used to assess total antibody titer and IgG isotype titer to the HA. High binding, 96-well polystyrene plates (Costar; Lowell, Mass., USA) were coated overnight with 50 ng/well of recombinant HA. Coating antigens were derived from the following representative viral isolates: A/Vietnam/1203/2004 (clade 1), A/Indonesia/5/2005 (clade 2.1), A/Whooper Swan/244/2005 (clade 2.2) and A/Anhui/1/2005 (clade 2.3). Plates were blocked with 5% milk diluted in PBS with 0.05% Tween 20 (blocking buffer). Serum samples were diluted in blocking buffer and added to plates. Serum was two-fold serially diluted and allowed to incubate for 1 hour at room temperature. Plates were washed and HRP-conjugated polyclonal goat anti-murine IgG, IgG1, IgG2a, IgG2b or IgG3 were diluted in blocking buffer and added to plates. Plates were incubated for 1 hour at room temperature, washed and HRP activity detected with TMB substrate (Sigma-Aldrich; St. Louis, Mo., USA). Plates were incubated in the dark for 15 minutes and then the reaction was stopped with 2N $H_2SO_4$. Optical densities at a wavelength of 450 nm ($OD_{450}$) were read by a spectrophotometer (BioTek; Winooski, Vt., USA) and end point dilution titers were determined. End point titers were determined as the reciprocal dilution of the last well, which had an $OD_{450}$ above the mean $OD_{450}$ plus two standard deviations of naïve animal sera.

Example 7—Hemagglutination Inhibition (HAI) Assay

The HAI assay was used to assess functional antibodies to the HA able to inhibit agglutination of horse erythrocytes. The protocol was adapted from the CDC laboratory-based influenza surveillance manual. To inactivate non-specific inhibitors, sera were treated with receptor destroying enzyme (RDE; Denka Seiken, Co., Japan) prior to being tested. Briefly, three parts RDE was added to one part sera and incubated overnight at 37° C. RDE was inactivated by incubation at 56° C. for about 30 min. RDE treated sera was two-fold serially diluted in v-bottom microtiter plates. An equal volume of each H5N1 virus, adjusted to approximately 8 HAU/50 µl, was added to each well. The plates were covered and incubated at room temperature for 20 min followed by the addition of 1% horse erythrocytes (HRBC) (Lampire Biologicals, Pipersville, Pa., USA) in PBS. Red blood cells were stored at 4° C. and used within 72 h of preparation. The plates were mixed by agitation, covered, and the RBCs were allowed to settle for 1 h at room temperature. The HAI titer was determined by the reciprocal dilution of the last well that contained non-agglutinated RBC. Positive and negative serum controls were included for each plate. All mice were negative (HAI less than or equal to 1:10) for pre-existing antibodies to currently circulating human influenza viruses prior to vaccination.

Example 8—Plaque Assay

Madin-Darby Canine Kidney (MDCK) cells were plated ($5\times10^5$) in each well of a 6-well plate. Samples were diluted (final dilution factors of $10^0$ to $10^{-6}$) and overlayed onto the cells in 100 µl of DMEM supplemented with penicillin-streptomycin and incubated for 1 hr. Samples were removed, cells were washed twice and media was replaced with 2 ml of L15 medium plus 0.8% agarose (Cambrex; East Rutherford, N.J., USA) and incubated for 72 h at 37° C. with 5% $CO_2$. Agarose was removed and discarded. Cells were fixed with 10% buffered formalin, and then stained with 1% crystal violet for 15 min. Following thorough washing in $dH_2O$ to remove excess crystal violet, plates were allowed to dry, plaques counted, and the plaque forming units (PFU)/ml were calculated.

Example 9—Statistical Analysis

Statistical significance of the antibody data was determined using a two-way analysis of variance (ANOVA) with Bonferroni's post-test to analyze differences between each vaccine group for the different test antigens (multiparametric). Differences in weight loss, sickness score, and viral titers were analyzed by two-way ANOVA, followed by Bonferroni's post-test for each vaccine group at multiple time points. Significance was defined as $p<0.05$. Statistical analyses were done using GraphPad Prism software.

Example 10—VLP Characterization of the Three H5N1 COBRA HA VLP Vaccines

Figure 3A:
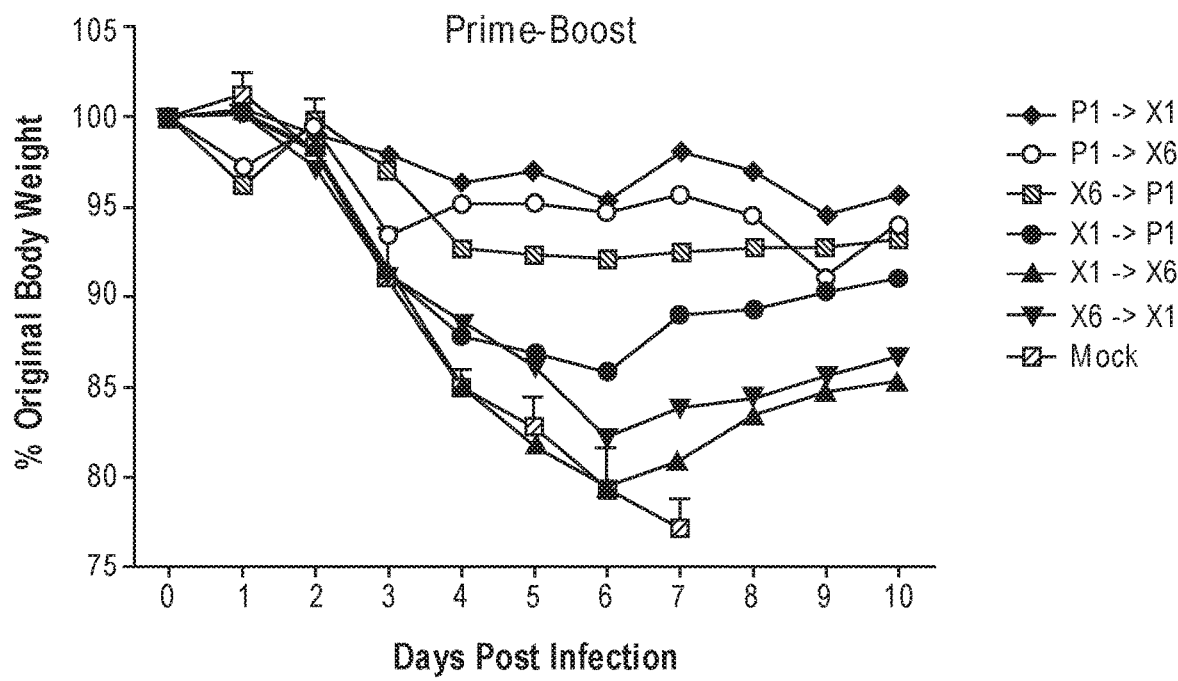
FIG. 3. Phylogenetic diversity of H5N1 influenza. The unrooted phylogenetic tree was inferred from HA amino acid sequences derived from 28 representative isolates in various clades and subclades and also the COBRA HA using the maximum likelihood method. Clade/subclade clusters are identified on the right. Sequences were aligned with MUSCLE 3.7 software and the alignment was refined by Gblocks 0.91b software. Phylogeny was determined using the maximum likelihood method with PhyML software. Trees were rendered using TreeDyn 198.3 software. The NCBI accession numbers for the HA sequences used in phylogeny inference were obtained through the Influenza Virus Resource.
Figure 3B:
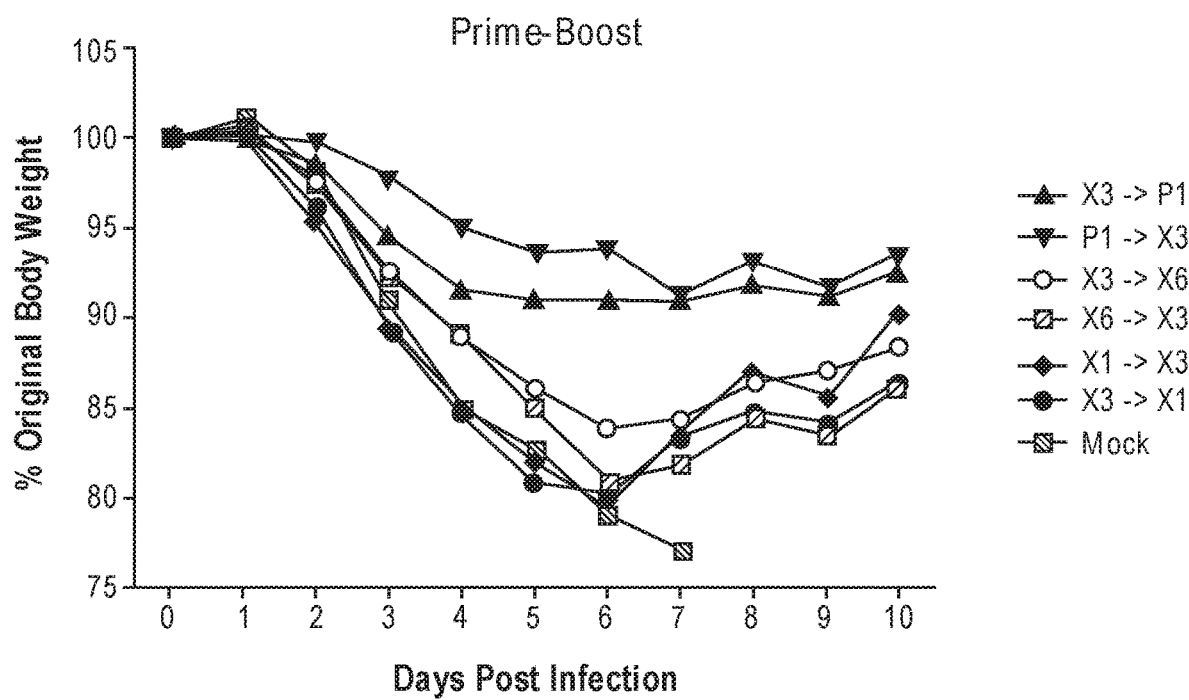
Figure 3C:
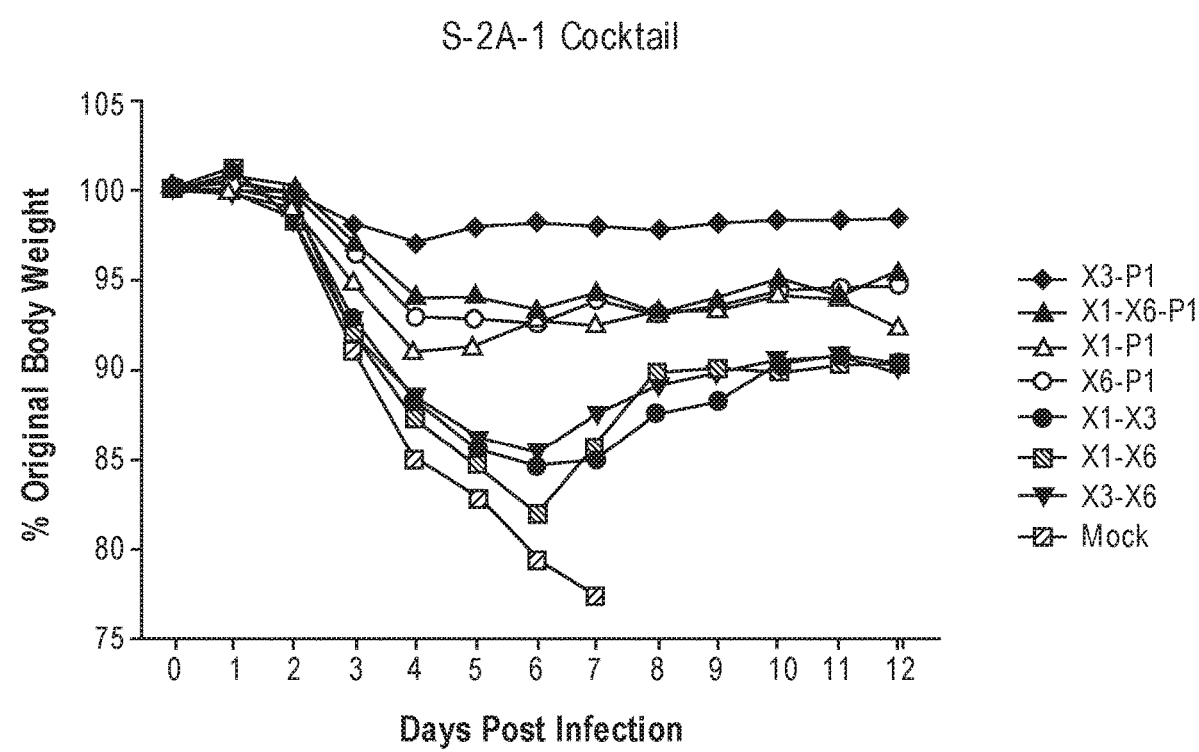

The design and characterization of the H5N1 computationally optimized broadly reactive antigen (COBRA) has been described previously (see, e.g., WO2012/036993 and WO2013/122827). Primary consensus sequences within each subclade were then aligned and the most common amino acid was chosen resulting in secondary consensus sequences representing each subclade (FIG. 1). The secondary consensus sequences were aligned and the most common amino acid at each position was selected resulting in the final consensus sequence referred to as clade 2 COBRA HA (FIG. 1). Using a predictive structural model of the three COBRA H5N1 HA sequences, three-dimensional trimerized HA proteins were designed (FIG. 2A). Despite nearly identical predicted structures, the COBRA HA proteins did have subtle differences in the major antigenic binding and receptor-binding sites. There were 11 amino acid positions that differed in at least one of the three H5N1 COBRA HA sequences (FIG. 2B). Phylogenetic analysis of the COBRA HA with all human isolates of H5N1 HA proteins (i.e., Human COBRA-2) indicated that COBRA retained a clade 2-like sequence without being grouped specifically within any clade 2 subclade cluster (FIG. 3). The Human/Avian COBRA 2 HA was more centrally located on the tree and was close to isolates in clade 8. In contrast, the third COBRA HA was generated using all sequences (All H5N1 COBRA) and was situated on the tree close to clades 5 and 9. Furthermore, a BLAST search using each of the COBRA HA sequences revealed that each sequence was a unique sequence that had not been isolated from the environment (data not shown).

Example 11—Challenge with Highly Pathogenic Avian Influenza (HPAI) H5N1 Viruses

Figure 4A:
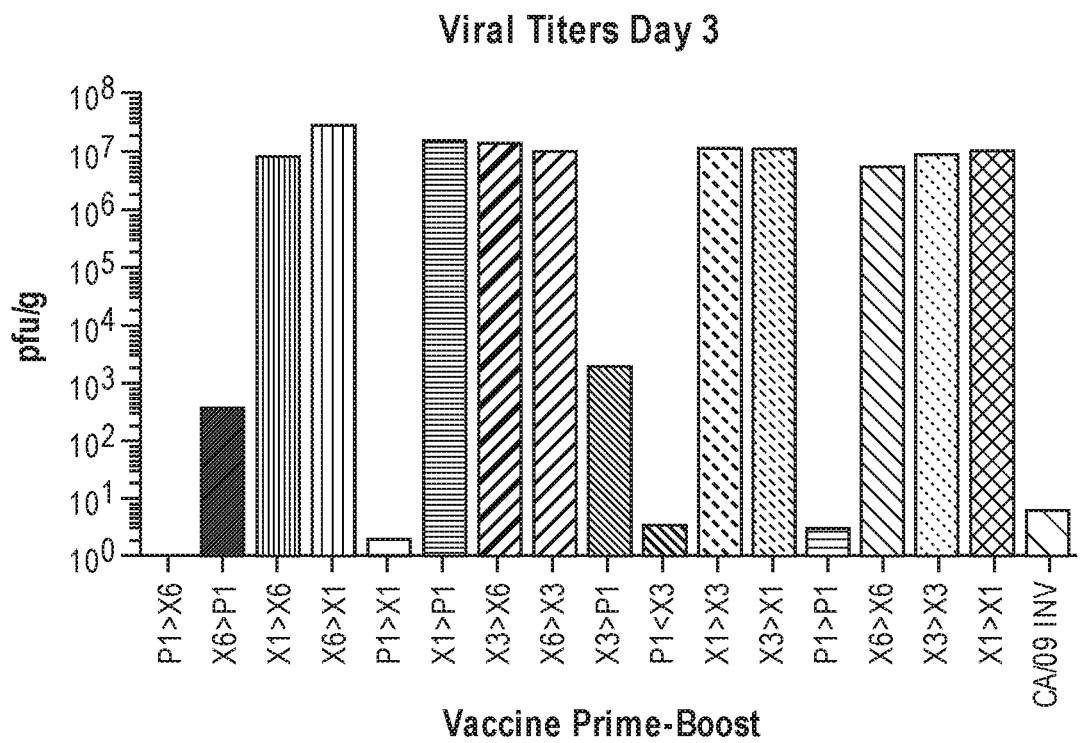
Figure 4B:
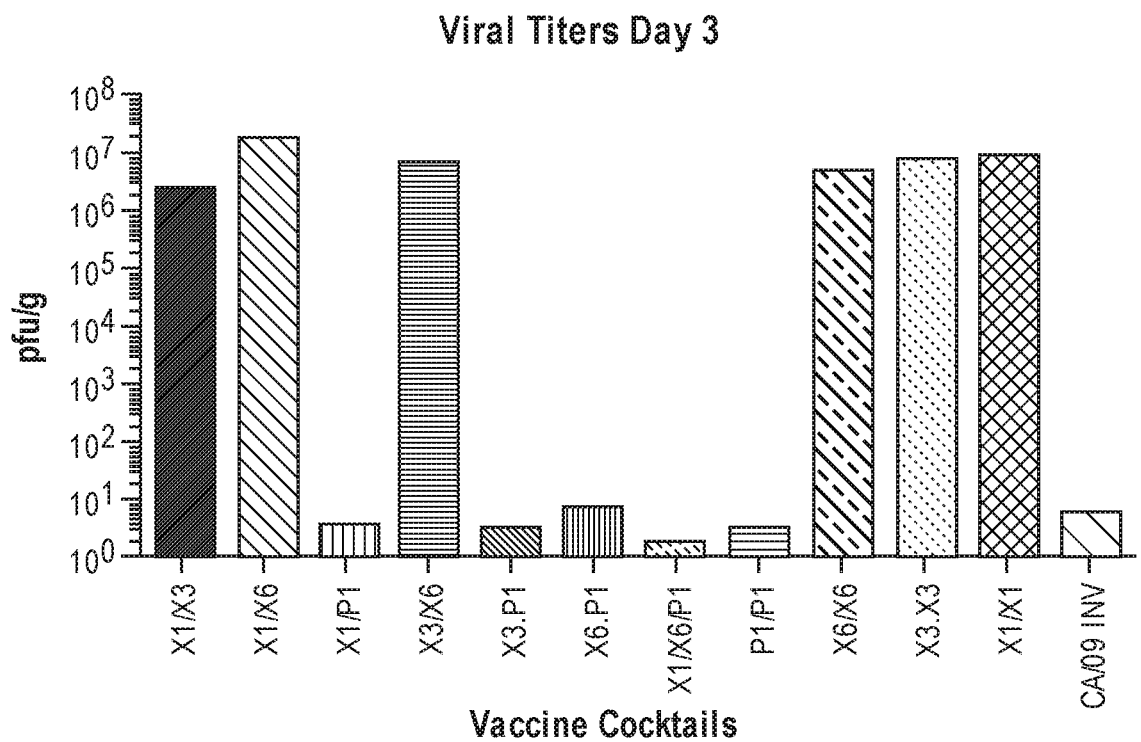

To determine the protective efficacy of each H5N1 COBRA vaccine, mice were vaccinated in different regimens at different doses and then challenged with highly pathogenic H5N1 viruses (FIG. 4). The first set of mice were vaccinated two times with a 3 µg dose (at week 0 and 4) and then were challenged (week 8) with a lethal dose ($5\times10^3$ PFU) of one of two the wild-type H5N1 viruses representing both major antigenic clusters (a clade 1 and a clade 2.1 isolate). All COBRA VLP-vaccinated mice and mice vaccinated with WS/05 VLPs were protected from weight loss and death, while mock-vaccinated animals rapidly lost weight and reached experimental endpoints between 6-9 days post-infection (DPI) (FIGS. 4A and C). All COBRA VLP-vaccinated mice failed to develop any overt signs of disease, while mock-vaccinated mice developed visible illness and had high viral titers in the lungs three days post-infection (FIGS. 4B and D).

A second set of mice were vaccinated with a single 3 µg dose of vaccine and challenged at week 8 with a lethal dose of A/Vietnam/1203/2004 ("VN/04"). Again, these mice had little or no weight loss, no clinical signs of disease, and no mortality (data not shown). However, the VN/04 virus was detected in the lungs of all mice (FIG. 5). On day 3, unvaccinated mice had an average viral titer in the lungs of 10e+6 pfu. Mice vaccinated with human COBRA-2 VLP or WS/05 VLP had 1.5 logs lower viral titer than unvaccinated mice (10e+4.5 pfu). Mice vaccinated with either of the second-generation COBRA vaccines had even lower viral titers between 10e+2.5 to 10e+3.5 pfu.

In order to differentiate the protective efficacy between the three vaccines, a third set of mice were vaccinated with a single half-log lower dose (0.6 μg) of each vaccine dose of each vaccine and challenged with either WS/05 or VN/04 viruses (FIG. 6). Once again, mock vaccinated mice rapidly lost weight to viral challenge and all mice succumb to disease between days 6-8 post-infection. Mice vaccinated with Human COBRA-2, All H5N1, or WS/05 VLPs and challenged with VN/04 virus had 5-8% weight loss between days 5-6 post-infection and then recovered (FIG. 6A). Mice vaccinated with the Human-Avian COBRA-2 VLPs had no weight loss and all mice survived infection. In contrast, mice challenged with the WS/05 virus suffered more severe weight loss regardless of vaccine used for immunization (FIG. 6B). Mice vaccinated with the All H5N1 COBRA vaccine lost between 15-20% of their weight by day 6 with 40% of the mice dying from infection. Mice vaccinated with any of the other three vaccines lost on average ~10% weight by day 6 following challenge with WS/05 virus.

In contrast to mice that received higher doses of vaccine or more than one vaccination, there was little to no detectable HAI titers against VN/04, WS/05, or Indo/05 viruses (data not shown). The lack of HAI activity and the increased weight loss directly translated into higher viral titers in the lungs of mice 2 and 3 days post-infection (FIGS. 6C and D). At day 3 post-infection, mock-vaccinated mice had 10e+6 pfu VN/04 viral titers in the lungs, which was similar to mice vaccinated with WS/05 VLP or the All H5N1 COBRA VLP vaccine (FIG. 6C). Mice vaccinated with human COBRA-2 or human/avian COBRA-2 had a log less VN/04 viral titers, albeit these viral titers were significantly higher than mice vaccinated with 3 ug mice (p>0.05). Vaccinated mice that were challenged with WS/05 virus had lower viral titers on day 2 and 3 post-infection than mice challenged with VN/04, with titers ranging from 10e+4.5 to 10e+5.5 pfu (FIG. 6D). WS/05 viral titers on day 3 were significantly lower in mice vaccinated with human COBRA-2 or human/avian COBRA-2 compared to mock vaccinated mice (FIG. 6D).

Example 12—VLPs Elicit Antibody Responses in Vaccinated Mice

In order to expand the breadth of antibody recognition, we developed second-generation H5N1 COBRA HA proteins to include epitopes from both human and avian isolates representing all clades of H5N1. BALB/c mice (n=12) were vaccinated twice at 4-week intervals via intramuscular injection with purified VLPs (3 μg based upon HA content) with one of the three H5N1 COBRA HA vaccines: Human COBRA-2, All H5N1 COBRA, or Human/Avian COBRA-2. At day 35, serum was analyzed for antibody responses. All vaccinated mice had high-titer anti-HA antibodies that bound to recombinant HA derived from both clade 1 and various subclades of clade 2 (data now shown). Although all three COBRA HA VLP vaccines elicited similar IgG titers, COBRA-vaccinated animals had higher HAI antibody titers for all viruses tested (P>0.001).

While both second generation COBRA HA proteins elicited antibodies that recognized similar numbers of H5N1 viruses compared to the first-generation Human COBRA-2 vaccine (9-11 out of 16 viruses), there were some unique differences in virus recognition by each COBRA HA antigen. H5N1 viruses can be grouped into three antigenic clusters with clades 0, 1, 3, 4, 5, 6, 7.1, and 9 as Antigenic Cluster 1 and subclades 2.2.1, 2.1.3.2, 2.3.4, 2.4, 2.5, and 8 into Antigenic Cluster 2. Viruses in subclade 2.3.2 and 7.2 stand as individual groups. The Human/Avian and All H5N1 COBRA HA antigens elicited antibodies with HAI activity against both clade 1 viruses (Table 3).

In contrast, only the human COBRA-2 HA elicited antibodies that recognized the clade 7 isolate. All three H5N1 COBRA HA antigens elicited HAI activity against the clade 2 viruses, Indo/05, Tk/05, Eg/07, Hubei/10, and both second generation HA vaccines also elicited antibodies that recognized VN/04, Tk/11, and Bng/11 isolates. In general, HAI titers appeared lower against viral isolates from 2011 and 2012, regardless which COBRA HA antigen was used for vaccination. (Table 3) The All H5N1 COBRA and Human COBRA-2 HA VLP vaccines elicited HAI activity against both clade 2.3.4 isolates. None of the vaccines elicited high HAI activity against the 2.3.2.1 cluster of viruses. (Table 3) The wild-type WS/05 HA VLP vaccine elicited low HAI titer antibodies to viruses isolated between 2004-2007, but did not recognize the other viruses isolated between 2008-2012. Overall, there was one virus, IN/12 (clade 2.1.3.2) that was not recognized by any of these COBRA HA VLP vaccines. Therefore, each individual COBRA HA VLP vaccine was able to elicit antibodies with a broader HAI activity against a larger number of H5N1 viruses from both antigenic clusters than VLP vaccines with a wild-type HA.

TABLE 3

| HAI Serum Antibody Titers From Mice Vaccinated Against a Panel of H5N1 Isolates | | | | | |
|---|---|---|---|---|---|
| | Human COBRA-2 | Human-Avian COBRA-2 | All H5 COBRA | WS/05 | Cocktail |
| Antigenic Cluster 1 | | | | | |
| Clade 1 (VN/1203/04) | 32 | 128 +/− 29* | 200 +/− 17* | 32 +/− 14 | 84 +/− 28* |
| Clade 1.1 (Cam/V0813302/11) | 5 +/− 0 | 25 +/− 0 | 42 +/− 28* | 5 +/− 0 | 42 +/− 14* |
| Clade 4 (Ck/Guiyang/846/06) | 5 +/− 0 | 5 +/− 0 | 45 +/− 10 | 5 +/− 0 | 49 +/− 9* |
| Clade 4 (Ck/HK/61.9/02) | 5 +/− 0 | 80 +/− 0* | 50 +/− 8* | 10 +/− 0 | 320 +/− 58* |
| Clade 4 (Gs/Fuj/bb/03) | 10 +/− 0 | 40 +/− 10 | 35 +/− 10 | 5 +/− 0 | 144 +/− 23* |
| Clade 5 (Dk/Guang/2291/04) | 5 +/− 0 | 10 +/− 0 | 20 +/− 0 | 5 +/− 0 | 344 +/− 56* |
| Clade 5 (Ck/Jilin/hq/03) | 5 +/− 0 | 10 +/− 0 | 50 +/− 15* | 20 +/− 0 | 160 +/− 29* |
| Clade 7 (Ck/VN/08) | 80 +/− 20 | 20 +/− 0 | 5 +/− 0 | 5 +/− 0 | 108 +/− 44 |
| Antigenic Cluster 2 | | | | | |
| Clade 2.1.3 (IN/05/05) | 100 +/− 10* | 128 +/− 36* | 40 +/− 0* | 16 +/− 0 | 656 +/− 354* |
| Clade 2.1.3.2 (IN/NIHRD1949/12) | 12 +/− 0 | 10 +/− 0 | 5 +/− 0 | 20 +/− 0 | 68 +/− 36 |

TABLE 3-continued

HAI Serum Antibody Titers From Mice Vaccinated Against a Panel of H5N1 Isolates

|  | Human COBRA-2 | Human-Avian COBRA-2 | All H5 COBRA | WS/05 | Cocktail |
|---|---|---|---|---|---|
| Clade 2.2 (WS/244/05) | 175 +/− 55* | 400 +/− 72* | 128 +/− 30* | 40 +/− 20 | 328 +/− 177* |
| Clade 2.2 (Tk/Tk/05) | 128 +/− 17* | 120 +/− 25* | 84 +/− 15* | 38 +/4 | 110 +/− 82 |
| Clade 2.2.1 (Egy/321/07) | 200 +/− 49* | 75 +/− 27* | 128 +/− 43* | 50 +/− 12 | 184 +/− 72* |
| Clade 2.2.1 (Egy/3300/08) | 50 +/− 9* | 10 +/− 2 | 5 +/− 0 | 5 +/− 0 | 108 +/− 44 |
| Clade 2.2.1 (Hubei/1/10) | 40 +/− 10 | 48 +/− 13 | 64 +/− 20* | 5 +/− 0 | 48 +/− 16 |
| Clade 2.2.1.1 (Tk/Isr/362/11) | 5 +/− 0 | 55 +/− 10 | 100 +/− 26* | 10 +/− 0 | 40 +/− 16 |
| Clade 2.2.2 (Bng/3233/11) | 20 +/− 0 | 64 +/− 13 | 128 +/− 0* | 20 +/− 0 | 44 +/− 17 |
| Clade 2.3.4 (AN/1/05) | 80 +/− 0* | 25 +/− 0 | 38 +/− 5 | 35 +/− 0 | 124 +/− 45* |
| Clade 2.3.4 (JWE/1038/06) | 80 +/− 15* | 20 +/− 0 | 75 +/− 25* | 30 +/− 0 | 152 +/− 67 |
| Individual Groups |  |  |  |  |  |
| Clade 2.3.2.1 (Egy/N02038/10) | 35 +/− 11 | 5 +/− 0 | 5 +/− 0 | 5 +/− 0 | 46 +/− 39 |
| Clade 2.3.2.1c (Dk/VN/LBM140/12) | 10 +/− 3 | 40 +/− 14 | 30 +/− 8 | 10 +/− 0 | 44 +/− 20 |
| Clade 2.3.2.1c (A/Alberta/1/2014) | 20 +/− 3 | 10 +/− 0 | 5 +/− 0 | 5 +/− 0 | 47 +/− 10 |
| Clade 7.2 (Ck/Ning/222/12) | 5 +/− 0 | 5 +/− 0 | 5 +/− 0 | 5 +/− 0 | 41 +/− 11 |

Example 13—A Cocktail of H5N1 COBRA HA VLPs Elicits Protective Antibody Responses Against H5N1 Isolates Since each of the three H5N1 COBRA HA proteins elicit HAI activity to different H5N1 viral strains, we decided to mix a cocktail of the three COBRA VLP vaccines together in order stimulate the broadest breadth of HAI activity against an expanded panel of 25 H5N1 isolates. Mice were vaccinated with 3 ug dose of each of the three H5N1 COBRA HA VLP vaccines intramuscularly at weeks 0 and 3. All mice vaccinated with the cocktail of H5N1 vaccines had HAI activity against the entire panel of 25 H5N1 viruses that were isolated from 2002-2014 (Table 3). These mice were protected against both weight loss and death following a lethal challenge using either VN/04 or WS/05 viruses and none of the COBRA VLP vaccinated mice had detectable viral titers (data not shown).

Example 14—Analysis

In this study, the immunogenicity and protective efficacy of three COBRA HA strategies proposed to increase breadth of antibody responses to a panel of H5N1 influenza viruses were compared. The COBRA HA antigens used in these studies were designed specifically to address the diversity present within clade 2, as well as across all clades of H5N1. Since it is not known which of the various strains from any clade or subclade of H5N1 circulating in bird populations may transform into a human transmissible influenza virus, designing vaccines to address all the potential strains from any clade of H5N1 is a prudent strategy. The Clade 2 specific COBRA HA proteins (COBRA-2 and Human/Avian COBRA-2) were generated using the genetically diverse clade 2 isolates. Clade 2 viruses are currently circulating widely in the Eastern Hemisphere. Clade 2 is divided into distinct subclades, including 2.1, 2.2, 2.3, 2.4, and 2.5, with some subclades being further divided into sub-subclades. Furthermore, within clade 2, humans have been infected with isolates representing clades 2.1, 2.2, and 2.3, with the recent human infections in Egypt identified as clade 2.2 and clade 2.1.3.2 infections in Bangladesh and southeast Asia. To generate a COBRA HA VLP vaccine for all isolates in the H5N1 influenza virus family, HA sequences from isolates representing all 10 clades were used for the All H5N1 COBRA HA vaccine. Each of the three COBRA HA antigens elicited HAI antibodies that recognized a similar number of H5N1 viruses in our panel (9-11 out of the initial 17). These titers were maintained for 72 weeks and these were protected against both VN/04 and WS/05 challenge with little weight loss or signs of morbidity (data not shown). However, individually, each of the COBRA HA VLP vaccines recognized a different set of viruses in the panel, with many of the viruses being recognized by antibodies elicited by at least one COBRA HA.

Some of the most difficult strains in our panel to recognize were detected with the COBRA antisera are part of the newly emerging sub-subclade in Southeast Asia. Beginning in 2011, an area from Bangladesh to Indonesia saw the introduction of these isolates into poultry, with some accompanying human infections and deaths. In 2007, clade 2.2 viruses were predominant in this region, but these viruses were replaced by the introduction of viruses from sub-subclades 2.3.2.1 and 2.3.4 in 2011. However, viruses in sub-subclade 2.3.2.1 are progressively replacing clade 2.2 and 2.3.4 viruses. In addition, there has been segment reassortment between H5N1 and H9N2 viruses circulating in Bangladesh, where H5N1 viruses are acquiring the PB1 gene from a H9N2 virus subtype. Point mutations have accumulated in these isolates over the last 5 years with potential modification of receptor binding and antigenic sites. The addition of these mutations may explain why these viruses were the most difficult viruses to detect with the elicited COBRA ferret antisera. If viruses in this sub-subclade are acquiring segments from H9N2 and additional mutations in HA enhance binding and entry into human cells, a human transmissible H5N1 isolate could emerge. Similar to the newly emerged H7N9 viruses in China that have killed 157 out of 448 cases (35% mortality rate) in two waves since early 2013. These H7N9 isolates contain gene segments from H9N2 with a viral phenotype that has low pathogenicity in poultry, but a high mortality rate in humans. The continued mutations of viruses in sub subclade 2.3.2.1, along with reassortment with H9N2 viruses, could result in a similar H5N1 phenotype.

While the three H5N1 COBRA VLP vaccines did not recognize all the viruses in the panel individually, collectively the three vaccines elicited a polyclonal antibody response that recognized all viruses in the panel. It was hypothesized that if all three COBRA HA VLP vaccines were mixed in a cocktail, the elicited antibody responses would recognize all isolates in the H5N1 viruses. There are structural changes between HA proteins within a clade and between different clades of H5N1 that may expose different epitopes on the HA molecule. Individually, the three H5N1 COBRA HA VLP vaccines elicited antibodies that neutralized different sets of H5N1 viruses in the panel based upon similarities in the structure of their HA molecules. The human COBRA-2 HA VLP vaccine had HAI activity against all the clade 2.1 and 2.2 isolates except those isolated in 2011 and 2012. The COBRA-2 HA has a similar structure around the receptor binding domain with specific residues that appear common in our different H5N1 COBRA HA sequences used in this study. All of the Clade 2 viruses isolated from 2005-2008 had similar antigenic structures. In contrast, the HA structures of the more recently isolated clade 2 viruses have a more closed receptor binding domain (RBD) that may indicate why COBRA-2 did not elicit antibodies that recognized this altered receptor binding domain. Both second-generation H5N1 COBRA HA VLP vaccines did elicit antibodies that did have HAI activity against these viruses from 2011, but not 2012 and they did not have HAI activity against Eg/08. Several additional examples can be identified from the empirical HAI titers determined in this study and the predicted HA structure, but in any case, once mice had been vaccinated simultaneously with all three H5N1 COBRA HA VLP vaccines, all 25 viruses in the panel were recognized in the HAI assay (Table 3).

The data presented in this report demonstrates that a cocktail of COBRA H5N1 HA proteins, presented to the immune system on a single VLP platform, can elicit cross-clade HAI activity that protects mice against challenge viruses from different clades over a 12-year span of time. Each of these COBRA HA antigens most likely elicits different sets of antibodies that bind to different antigenic regions of the HA molecule, but when administered together as a cocktail, they elicit antibodies that recognize divergent HA head epitopes that synergistically neutralize viral infection.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. An immunogenic composition comprising a combination of at least two recombinant H5N1 influenza hemagglutinin (HA) polypeptides selected from the group consisting of: a recombinant influenza HA polypeptide comprising the amino acid sequence of SEQ ID NO: 1, a recombinant influenza HA polypeptide comprising the amino sequence of SEQ ID NO: 3, and a recombinant influenza HA polypeptide comprising the amino sequence of SEQ ID NO: 5.

2. The immunogenic composition of claim 1, wherein the composition comprises a combination of recombinant H5N1 influenza HA polypeptides consisting of a recombinant influenza HA polypeptide comprising the amino acid sequence of SEQ ID NO: 1 and a recombinant influenza HA polypeptide comprising the amino sequence of SEQ ID NO: 3.

3. The immunogenic composition of claim 1, wherein the composition comprises a combination of recombinant H5N1 influenza HA polypeptides consisting of a recombinant influenza HA polypeptide comprising the amino acid sequence of SEQ ID NO: 1 and a recombinant influenza HA polypeptide comprising the amino sequence of SEQ ID NO: 5.

4. The immunogenic composition of claim 1, wherein the composition comprises a combination of recombinant H5N1 influenza HA polypeptides consisting of a recombinant influenza HA polypeptide comprising the amino sequence of SEQ ID NO: 3 and a recombinant influenza HA polypeptide comprising the amino sequence of SEQ ID NO: 5.

5. The immunogenic composition of claim 1, wherein the composition comprises a combination of three recombinant H5N1 influenza HA polypeptides selected from the group consisting of: a recombinant influenza HA polypeptide comprising the amino acid sequence of SEQ ID NO: 1; a recombinant influenza HA polypeptide comprising the amino sequence of SEQ ID NO: 3; and a recombinant influenza HA polypeptide comprising the amino sequence of SEQ ID NO: 5.

6. The immunogenic composition of claim 1, wherein at least one of the recombinant influenza HA polypeptides lacks the N-terminal methionine residue.

7. An immunogenic composition comprising a combination of at least two recombinant H5N1 influenza hemagglutinin (HA) polypeptides selected from the group consisting of: a recombinant influenza HA polypeptide comprising the amino acid sequence of residues 2-566 of SEQ ID NO: 1, a recombinant influenza HA polypeptide comprising the amino acid sequence of residues 2-567 of SEQ ID NO: 3, and a recombinant influenza HA polypeptide comprising the amino sequence of residues 2-568 of SEQ ID NO: 5.

8. The immunogenic composition of claim 7, wherein the composition comprises a combination of recombinant H5N1 influenza HA polypeptides consisting of a recombinant influenza HA polypeptide comprising the amino acid sequence of residues 2-566 of SEQ ID NO: 1 and a recombinant influenza HA polypeptide comprising the amino acid sequence of residues 2-567 of SEQ ID NO: 3.

9. The immunogenic composition of claim 7, wherein the composition comprises a combination of recombinant H5N1 influenza HA polypeptides consisting of a recombinant influenza HA polypeptide comprising the amino acid sequence of residues 2-566 of SEQ ID NO: 1 and a recombinant influenza HA polypeptide comprising the amino sequence of residues 2-568 of SEQ ID NO: 5.

10. The immunogenic composition of claim 7, wherein the composition comprises a combination of recombinant H5N1 influenza HA polypeptides consisting of a recombinant influenza HA polypeptide comprising the amino acid sequence of residues 2-567 of SEQ ID NO: 3 and a recombinant influenza HA polypeptide comprising the amino sequence of residues 2-568 of SEQ ID NO: 5.

11. The immunogenic composition of claim 7, wherein the composition comprises a combination of three recombinant H5N1 influenza HA polypeptides selected from the group consisting of: a recombinant influenza HA polypeptide comprising the amino acid sequence of residues 2-566 of SEQ ID NO: 1; a recombinant influenza HA polypeptide comprising the amino acid sequence of residues 2-567 of SEQ ID NO: 3; and a recombinant influenza HA polypeptide comprising the amino sequence of residues 2-568 of SEQ ID NO: 5.

12. The immunogenic composition of claim 1, wherein the recombinant H5N1 influenza HA polypeptides are presented on virus-like particles (VLPs).

13. The immunogenic composition of claim 1, wherein the recombinant H5N1 influenza HA polypeptides are presented on an inactivated influenza virus.

14. The immunogenic composition of claim 13, wherein the inactivated influenza virus is a whole virus.

15. The immunogenic composition of claim 13, wherein the inactivated influenza virus is a split virus.

16. The immunogenic composition of claim 1, wherein the immunogenic composition further comprises an adjuvant.

17. A method for prophylaxis of influenza infection or disease in a subject, the method comprising administering an immunogenic composition of claim 1 to the subject.

18. A method for prophylaxis of influenza infection or disease in a subject, the method comprising co-administering at least two recombinant H5N1 influenza hemagglutinin (HA) polypeptides selected from the group consisting of: a recombinant influenza HA polypeptide comprising the amino acid sequence of SEQ ID NO: 1, a recombinant influenza HA polypeptide comprising the amino sequence of SEQ ID NO: 3, and a recombinant influenza HA polypeptide comprising the amino sequence of SEQ ID NO: 5.

19. The method of claim 18, wherein at least two recombinant H5N1 influenza hemagglutinin (HA) polypeptides are co-administered at the same time.

20. The method of claim 19, wherein the at least two recombinant H5N1 influenza hemagglutinin (HA) polypeptides are co-administered sequentially.

21. The method of claim 18, wherein the immunogenic composition or the at least two recombinant H5N1 influenza hemagglutinin (HA) polypeptides are administered to the subject by intradermal, intranasal, intramuscular, oral, or subcutaneous delivery.

22. The method of claim 18, wherein the subject is human.

23. The method of claim 18, wherein the immunogenic composition or the at least two recombinant H5N1 influenza hemagglutinin (HA) polypeptides elicit a hemagglutination-inhibition (HAI) antibody titer of at least 1:40 in the subject.

* * * * *